US010378063B2

(12) United States Patent
Stransky et al.

(10) Patent No.: US 10,378,063 B2
(45) Date of Patent: Aug. 13, 2019

(54) RAF1 FUSIONS

(71) Applicant: BLUEPRINT MEDICINES CORPORATION, Cambridge, MA (US)

(72) Inventors: Nicolas Stransky, Charlestown, MA (US); Joseph L. Kim, Wayland, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 15/317,685

(22) PCT Filed: Jun. 10, 2015

(86) PCT No.: PCT/US2015/035019
§ 371 (c)(1),
(2) Date: Dec. 9, 2016

(87) PCT Pub. No.: WO2015/191666
PCT Pub. Date: Dec. 17, 2015

(65) Prior Publication Data

US 2017/0137889 A1 May 18, 2017

Related U.S. Application Data

(60) Provisional application No. 62/010,242, filed on Jun. 10, 2014.

(51) Int. Cl.
*C12Q 1/68* (2018.01)
*C07H 21/04* (2006.01)
*C12Q 1/6886* (2018.01)
*C07K 16/32* (2006.01)
*G01N 33/574* (2006.01)

(52) U.S. Cl.
CPC ............ *C12Q 1/6886* (2013.01); *C07K 16/32* (2013.01); *G01N 33/5748* (2013.01); *C07K 2317/33* (2013.01); *C07K 2317/34* (2013.01); *C12Q 2600/106* (2013.01); *C12Q 2600/118* (2013.01); *C12Q 2600/156* (2013.01); *G01N 2333/91205* (2013.01)

(58) Field of Classification Search
None
See application file for complete search history.

(56) References Cited

FOREIGN PATENT DOCUMENTS

WO WO 2014/071419 A2 5/2014
WO WO 2014/172046 A2 10/2014

OTHER PUBLICATIONS

International Patent Application No. PCT/US20151035019, filed Jun. 10, 2015, by Blueprint Medicines Corp.: International Search Report and Written Opinion, dated Feb. 26, 2016 (16 pages).

(Continued)

*Primary Examiner* — Jeanine A Goldberg
(74) *Attorney, Agent, or Firm* — Finnegan, Henderson, Farabov Garrett & Dunner, LLP

(57) ABSTRACT

The invention provides to RAF1 gene fusions, RAF1 fusion proteins, and fragments of those genes and polypeptides. The invention further provides methods of diagnosing and treating diseases or disorders associated with RAF1 fusions, such as conditions mediated by aberrant RAF1 expression or activity, or overexpression of RAF1.

6 Claims, 13 Drawing Sheets

Specification includes a Sequence Listing.

```
ATGGCCTCGG AGGCGCCGTC CCCGCCGCGG TCGCCGCCGC CGCCCACCTC CCCCGAGCCT   60
GAGCTGGCCC AGCTAAGGCG GAAGGTGGAG AAGTTGGAAC GTGAACTGCG GAGCTGCAAG  120
CGGCAGGTGC GGGAGATCGA GAAGCTGCTG CATCACACAG AACGGCTGTA CCAGAACGCA  180
GAAAGCAACA ACCAGGAGCT CCGCACGCAG GTGGAAGAAC TCAGTAAAAT ACTCCAACGT  240
GGGAGAAATG AAGATAATAA AAAGTCTGAT GTAGAAGTAC AAACAGAGAA CCATGCTCCT  300
TGGTCAATCT CAGATTATTT TTATCAGACG TACTACAATG ACGTTAGTCT TCCAAATAAA  360
GTGACTGAAC TGTCAGATCA ACAAGATCAA GCTATCGAAA CTTCTATTTT GAATTCTAAA  420
GACCATTTAC AAGTAGAAAA TGATGCTTAC CCTGGTACCG ATAGAACAGA AAATGTTAAA  480
TATAGACAAG TGGACCATTT TGCCTCAAAT TCACAGGAGC CAGCATCTGC ATTAGCAACA  540
GAAGATACCT CCTTAGAAGG CTCATCATTA GCTGAAAGTT TGAGAGCTGC AGCAGAAGCG  600
GCTGTATCAC AGACTGGATT TAGTTATGAT GAAAATACTG GACTGTATTT TGACCACAGC  660
ACTGGTTTCT ATTATGATTC TGAAAATCAA CTCTATTATG ATCCTTCCAC TGGAATTTAT  720
TACTATTGTG ATGTGGAAAG TGGTCGTTAT CAGTTTCATT CTCGAGTAGA TTTGCAACCT  780
TATCCGACTT CTAGCACAAA ACAAAGTAAA GATAAAAAAT TGAAGAAGAA AAGAAAAGAT  840
CCAGATTCTT CTGCAACAAA TGAGGAAAAG/GATGCAATTC GAAGTCACAG CGAATCAGCC  900
TCACCTTCAG CCCTGTCCAG TAGCCCCAAC AATCTGAGCC CAACAGGCTG GTCACAGCCG  960
AAAACCCCCG TCCCAGCACA AAGAGAGCGG GCACCAGTAT CTGGCACCCA GGAGAAAAAC 1020
AAAATTAGGC CTCGTGGACA GAGAGATTCA AGCTATTATT GGGAAATAGA AGCCAGTGAA 1080
GTGATGCTGT CCACTCGGAT TGGGTCAGGC TCTTTTGGAA CTGTTTATAA GGGTAAATGG 1140
CACGGAGATG TTGCAGTAAA GATCCTAAAG GTTGTCGACC CAACCCCAGA GCAATTCCAG 1200
GCCTTCAGGA ATGAGGTGGC TGTTCTGCGC AAAACACGGC ATGTGAACAT TCTGCTTTTC 1260
ATGGGGTACA TGACAAAGGA CAACCTGGCA ATTGTGACCC AGTGGTGCGA GGGCAGCAGC 1320
CTCTACAAAC ACCTGCATGT CCAGGAGACC AAGTTTCAGA TGTTCCAGCT AATTGACATT 1380
GCCCGGCAGA CGGCTCAGGG AATGGACTAT TTGCATGCAA AGAACATCAT CCATAGAGAC 1440
ATGAAATCCA ACAATATATT TCTCCATGAA GGCTTAACAG TGAAAATTGG AGATTTTGGT 1500
TTGGCAACAG TAAAGTCACG CTGGAGTGGT TCTCAGCAGG TTGAACAACC TACTGGCTCT 1560
GTCCTCTGGA TGGCCCCAGA GGTGATCCGA ATGCAGGATA ACAACCCATT CAGTTTCCAG 1620
TCGGATGTCT ACTCCTATGG CATCGTATTG TATGAACTGA TGACGGGGGA GCTTCCTTAT 1680
TCTCACATCA ACAACCGAGA TCAGATCATC TTCATGGTGG GCCGAGGATA TGCCTCCCCA 1740
GATCTTAGTA ACCTATATAA CAACTGCCCC AAACCAATGA AGACCCTCCT AGCTGACTGT 1800
GTGAAGAAAG TAAAGGAAGA GAGGCCTCTT TTTCCCCAGA TCCTGTCTTC CATTGAGCTG 1860
CTCCAACACT CTCTACCGAA GATCAACCGG AGCGCTTCCG AGCCATCCTT GCATCGGGCA 1920
GCCCACACTG AGGATATCAA TGCTTGCACG CTGACCACGT CCCCGAGGCT GCCTGTCTTC 1980
TAG

                                                      (SEQ ID NO:1)
```

(56) References Cited

OTHER PUBLICATIONS

Genbank Database Accession No. NM_001286, "*Homo sapiens* chloride voltage-gated channel 6 (CLCN6), transcript variant 1, mRNA", National Center for Biotechnology information (NCBI), U.S. National Library of Medicine; PRI Oct. 7, 2016 (9 pages).
Genbank Database Accession No. NM_002880, "*Homo sapiens* Raf-1 proto-oncogene, serine/threonine kinase (RAF1), mRNA", National Center for Biotechnology Information (NCBI), U.S. National Library of Medicine; PRI Oct. 6, 2016 (9 pages).
Genbank Database Accession No. 006999, "*Homo sapiens* poly(A) RNA polymerase D7, non-canonical (PAPD7), transcript variant 1, mRNA", National Center for Biotechnology Information (NCBI), U.S. National Library of Medicine; PRI Oct. 6, 2016 (5 pages).
Genbank Database Accession No. NM_170707, "*Homo sapiens* lamin A/C (LMNA), transcript variant 1, MRNA", National Center for Biotechnology Information (NCBI), U.S. National Library of Medicine; PRI Oct. 26, 2016 (18 pages).
Genbank Database Accession No. NM_018046, "*Homo sapiens* angiogenic factor with G-patch and FHA domains 1 (AGGF1), mRNA", National Center for Biotechnology information (NCBI), U.S. National Library of Medicine; PRI Apr. 28, 2016 (6 pages).
Genbank Database Accession No. NM_201274, "*Homo sapiens* myosin phosphatase Rho interacting protein (MPRIP), transcript variant 2, mRNA", National Center for Biotechnology Information (NCBI), U.S. National Library of Medicine; PRI Sep. 10, 2016 (12 pages).
Genbank Database Accession No. NM_001042646, "*Homo sapiens* trafficking kinesin protein 1 (TRAK1), transcript variant 1, mRNA", National Center for Biotechnology Information (NCBI), U.S. National Library of Medicine; PRI Mar. 9, 2017 (6 pages).
Soda, Manabu, et al., "Identification of the transforming EML4-ALK fusion gene in non-small-cell lung cancer," Nature, 448:561-567 (2007).
Giacomini, Craig P., et al., "Breakpoint Analysis of Transcriptional and Genomic Profiles Uncovers Novel Gene Fusions Spanning Multiple Human Cancer Types", *PLOS Genetics*, 9(4):e1003464 (19 pages) (2013).
Lawson, Andrew R., et al., "RAF gene fusions are specific to pilocytic astrocytoma in a broad paediatric brain tumour cohort", *Acta Neuropathol*, 120:271-273 (2010).
Al Obaidi, L., et al., RAF Fusion Transcripts Detected in Medulloblastoma but not Ependymoma Using RT-RQPCR Assays on RNA isolated From FFPE Tissues, *European Journal of Cancer*, 48(Suppl. 5):S130, Abstract 549 (2012).

FIG. 1

```
ATGGCCTCGG AGGCGCCGTC CCCGCCGCGG TCGCCGCCGC CGCCCACCTC CCCCGAGCCT   60
GAGCTGGCCC AGCTAAGGCG GAAGGTGGAG AAGTTGGAAC GTGAACTGCG GAGCTGCAAG  120
CGGCAGGTGC GGGAGATCGA GAAGCTGCTG CATCACACAG AACGGCTGTA CCAGAACGCA  180
GAAAGCAACA ACCAGGAGCT CCGCACGCAG GTGGAAGAAC TCAGTAAAAT ACTCCAACGT  240
GGGAGAAATG AAGATAATAA AAAGTCTGAT GTAGAAGTAC AAACAGAGAA CCATGCTCCT  300
TGGTCAATCT CAGATTATTT TTATCAGACG TACTACAATG ACGTTAGTCT TCCAAATAAA  360
GTGACTGAAC TGTCAGATCA ACAAGATCAA GCTATCGAAA CTTCTATTTT GAATTCTAAA  420
GACCATTTAC AAGTAGAAAA TGATGCTTAC CCTGGTACCG ATAGAACAGA AAATGTTAAA  480
TATAGACAAG TGGACCATTT TGCCTCAAAT TCACAGGAGC CAGCATCTGC ATTAGCAACA  540
GAAGATACCT CCTTAGAAGG CTCATCATTA GCTGAAAGTT TGAGAGCTGC AGCAGAAGCG  600
GCTGTATCAC AGACTGGATT TAGTTATGAT GAAAATACTG GACTGTATTT TGACCACAGC  660
ACTGGTTTCT ATTATGATTC TGAAAATCAA CTCTATTATG ATCCTTCCAC TGGAATTTAT  720
TACTATTGTG ATGTGGAAAG TGGTCGTTAT CAGTTTCATT CTCGAGTAGA TTTGCAACCT  780
TATCCGACTT CTAGCACAAA ACAAAGTAAA GATAAAAAAT TGAAGAAGAA AAGAAAAGAT  840
CCAGATTCTT CTGCAACAAA TGAGGAAAAG/GATGCAATTC GAAGTCACAG CGAATCAGCC  900
TCACCTTCAG CCCTGTCCAG TAGCCCCAAC AATCTGAGCC CAACAGGCTG GTCACAGCCG  960
AAAACCCCCG TGCCAGCACA AAGAGAGCGG GCACCAGTAT CTGGGACCCA GGAGAAAAAC 1020
AAAATTAGGC CTCGTGGACA GAGAGATTCA AGCTATTATT GGGAAATAGA AGCCAGTGAA 1080
GTGATGCTGT CCACTCGGAT TGGGTCAGGC TCTTTTGGAA CTGTTTATAA GGGTAAATGG 1140
CACGGAGATG TTGCAGTAAA GATCCTAAAG GTTGTCGACC CAACCCCAGA GCAATTCCAG 1200
GCCTTCAGGA ATGAGGTGGC TGTTCTGCGC AAAACACGGC ATGTGAACAT TCTGCTTTTC 1260
ATGGGGTACA TGACAAAGGA CAACCTGGCA ATTGTGACCC AGTGGTGCGA GGGCAGCAGC 1320
CTCTACAAAC ACCTGCATGT CCAGGAGACC AAGTTTCAGA TGTTCCAGCT AATTGACATT 1380
GCCCGGCAGA CGGCTCAGGG AATGGACTAT TTGCATGCAA AGAACATCAT CCATAGAGAC 1440
ATGAAATCCA ACAATATATT TCTCCATGAA GGCTTAACAG TGAAAATTGG AGATTTTGGT 1500
TTGGCAACAG TAAAGTCACG CTGGAGTGGT TCTCAGCAGG TTGAACAACC TACTGGCTCT 1560
GTCCTCTGGA TGGCCCCAGA GGTGATCCGA ATGCAGGATA ACAACCCATT CAGTTTCCAG 1620
TCGGATGTCT ACTCCTATGG CATCGTATTG TATGAACTGA TGACGGGGGA GCTTCCTTAT 1680
TCTCACATCA ACAACCGAGA TCAGATCATC TTCATGGTGG GCCGAGGATA TGCCTCCCCA 1740
GATCTTAGTA AGCTATATAA GAACTGCCCC AAAGCAATGA AGAGGCTGGT AGCTGACTGT 1800
GTGAAGAAAG TAAAGGAAGA GAGGCCTCTT TTTCCCCAGA TCCTGTCTTC CATTGAGCTG 1860
CTCCAACACT CTCTACCGAA GATCAACCGG AGCGCTTCCG AGCCATCCTT GCATCGGGCA 1920
GCCCACACTG AGGATATCAA TGCTTGCACG CTGACCACGT CCCCGAGGCT GCCTGTCTTC 1980
TAG
```

(SEQ ID NO:1)

FIG. 2

MASEAPSPPR SPPPPTSPEP ELAQLRRKVE KLERELRSCK RQVREIEKLL HHTERLYQNA 60
ESNNQELRTQ VEELSKILQR GRNEDNKKSD VEVQTENHAP WSISDYFYQT YYNDVSLPNK 120
VTELSDQQDQ AIETSILNSK DHLQVENDAY PGTDRTENVK YRQVDHFASN SQEPASALAT 180
EDTSLEGSSL AESLRAAAEA AVSQTGFSYD ENTGLYFDHS TGFYYDSENQ LYYDPSTGIY 240
YYCDVESGRY QFHSRVDLQP YPTSSTKQSK DKKLKKKRKD PDSSATNEEK/DAIRSHSESA 300
SPSALSSSPN NLSPTGWSQP KTPVPAQRER APVSGTQEKN KIRPRGQRDS SYYWEIEASE 360
VMLSTRIGSG SFGTVYKGKW HGDVAVKILK VVDPTPEQFQ AFRNEVAVLR KTRHVNILLF 420
MGYMTKDNLA IVTQWCEGSS LYKHLHVQET KFQMFQLIDI ARQTAQGMDY LHAKNIIHRD 480
MKSNNIFLHE GLTVKIGDFG LATVKSRWSG SQQVEQPTGS VLWMAPEVIR MQDNNPFSFQ 540
SDVYSYGIVL YELMTGELPY SHINNRDQII FMVGRGYASP DLSKLYKNCP KAMKRLVADC 600
VKKVKEERPL FPQILSSIEL LQHSLPKINR SASEPSLHRA AHTEDINACT LTTSPRLPVF 660

(SEQ ID NO:2)

FIG. 3

ATGGAGACCC CGTCCCAGCG GCGCGCCACC CGCAGCGGGG CGCAGGCCAG CTCCACTCCG 60
CTGTCGCCCA CCCGCATCAC CCGGCTGCAG GAGAAGGAGG ACCTGCAGGA GCTCAATGAT 120
CGCTTGGCGG TCTACATCGA CCGTGTGCGC TCGCTGGAAA CGGAGAACGC AGGGCTGCGC 180
CTTCGCATCA CCGAGTCTGA AGAGGTGGTC AGCCGCGAGG TGTCCGGCAT CAAGGCCGCC 240
TACGAGGCCG AGCTCGGGGA TGCCCGCAAG ACCCTTGACT CAGTAGCCAA GGAGCGCGCC 300
CGCCTGCAGC TGGAGCTGAG CAAAGTGCGT GAGGAGTTTA AGGAGCTGAA AGCGCGCAAT 360
ACCAAGAAGG AGGGTGACCT GATAGCTGCT CAGGCTCGGC TGAAGGACCT GGAGGCTCTG 420
CTGAACTCCA AGGAGGCCGC ACTGAGCACT GCTCTCAGTG AGAAGCGCAC GCTGGAGGGC 480
GAGCTGCATG ATCTGCGGGG CCAGGTGGCC AAGCTTGAGG CAGCCCTAGG TGAGGCCAAG 540
AAGCAACTTC AGGATGAGAT GCTGCGGCGG GTGGATGCTG AGAACAGGCT GCAGACCATG 600
AAGGAGGAAC TGGACTTCCA GAAGAACATC TACAGTGAGG AGCTGCGTGA GACCAAGCGC 660
CGTCATGAGA CCCGACTGGT GGAGATTGAC AATGGGAAGC AGCGTGAGTT TGAGAGCCGG 720
CTGGCGGATG CGCTGCAGGA ACTGCGGGCC CAGCATGAGG ACCAGGTGGA GCAGTATAAG 780
AAGGAGCTGG AGAAGACTTA TTCTGCCAAG CTGGACAATG CCAGGCAGTC TGCTGAGAGG 840
AACAGCAACC TGGTGGGGGC TGCCCACGAG GAGCTGCAGC AGTCGCGCAT CCGCATCGAC 900
AGCCTCTCTG CCCAGCTCAG CCAGCTCCAG AAGCAGCTGG CAGCCAAGGA GGCGAAGCTT 960
CGAGACCTGG AGGACTCACT GGCCCGTGAG CGGGACACCA GCCGGCGGCT GCTGGCGGAA 1020
AAGGAGCGGG AGATGGCCGA GATGCGGGCA AGGATGCAGC AGCAGCTGGA CGAGTACCAG 1080
GAGCTTCTGG ACATCAAGCT GGCCCTGGAC ATGGAGATCC ACGCCTACCG CAAGCTCTTG 1140
GAGGGCGAGG AGGAGAGGCT ACGCCTGTCC CCCAGCCCTA CCTCGCAGCG CAGCCGTGGC 1200
CGTGCTTCCT CTCACTCATC CCAGACACAG GGTGGGGGCA GCGTCACCAA AAAGCGCAAA 1260
CTGGAGTCCA CTGAGAGCCG CAGCAGCTTC TCACAGCACG CACGCACTAG CGGGCGCGTG 1320
GCCGTGGAGG AGGTGGATGA GGAGGGCAAG TTTGTCCGGC TGCGCAACAA GTCCAATGAG 1380
GACCAGTCCA TGGGCAATTG GCAGATCAAG CGCCAGAATG GAGATGATCC CTTGCTGACT 1440
TACCGGTTCC CACCAAAGTT CACCCTGAAG GCTGGGCAGG TGGTGACGAT CTGGGCTGCA 1500
GGAGCTGGGG CCACCCACAG CCCCCCTACC GACCTGGTGT GGAAGGCACA GAACACCTGG 1560
GGCTGCGGGA ACAGCCTGCG TACGGCTCTC ATCAACTCCA CTGGGGAAGA AGTGGCCATG 1620
CGCAAGCTGG TGCGCTCAGT GACTGTGGTT GAGGACGACG AGGATGAGGA TGGAGATGAC 1680
CTGCTCCATC ACCACCAC/GA TGCAATTCGA AGTCACAGCG AATCAGCCTC ACCTTCAGCC 1740
CTGTCCAGTA GCCCCAACAA TCTGAGCCCA ACAGGCTGGT CACAGCCGAA AACCCCCGTG 1800
CCAGCACAAA GAGAGCGGGC ACCAGTATCT GGGACCCAGG AGAAAAACAA AATTAGGCCT 1860
CGTGGACAGA GAGATTCAAG CTATTATTGG GAAATAGAAG CCAGTGAAGT GATGCTGTCC 1920
ACTCGGATTG GGTCAGGCTC TTTTGGAACT GTTTATAAGG GTAAATGGCA CGGAGATGTT 1980
GCAGTAAAGA TCCTAAAGGT TGTCGACCCA ACCCCAGAGC AATTCCAGGC CTTCAGGAAT 2040
GAGGTGGCTG TTCTGCGCAA AACACGGCAT GTGAACATTC TGCTTTTCAT GGGGTACATG 2100
ACAAAGGACA ACCTGGCAAT TGTGACCCAG TGGTGCGAGG GCAGCAGCCT CTACAAACAC 2160
CTGCATGTCC AGGAGACCAA GTTTCAGATG TTCCAGCTAA TTGACATTGC CCGGCAGACG 2220
GCTCAGGGAA TGGACTATTT GCATGCAAAG AACATCATCC ATAGAGACAT GAAATCCAAC 2280
AATATATTTC TCCATGAAGG CTTAACAGTG AAAATTGGAG ATTTTGGTTT GGCAACAGTA 2340
AAGTCACGCT GGAGTGGTTC TCAGCAGGTT GAACAACCTA CTGGCTCTGT CCTCTGGATG 2400
GCCCCAGAGG TGATCCGAAT GCAGGATAAC AACCCATTCA GTTTCCAGTC GGATGTCTAC 2460
TCCTATGGCA TCGTATTGTA TGAACTGATG ACGGGGGAGC TTCCTTATTC TCACATCAAC 2520
AACCGAGATC AGATCATCTT CATGGTGGGC CGAGGATATG CCTCCCCAGA TCTTAGTAAG 2580
CTATATAAGA ACTGCCCCAA AGCAATGAAG AGGCTGGTAG CTGACTGTGT GAAGAAAGTA 2640
AAGGAAGAGA GGCCTCTTTT TCCCCAGATC CTGTCTTCCA TTGAGCTGCT CCAACACTCT 2700
CTACCGAAGA TCAACCGGAG CGCTTCCGAG CCATCCTTGC ATCGGGCAGC CCACACTGAG 2760
GATATCAATG CTTGCACGCT GACCACGTCC CCGAGGCTGC CTGTCTTCTA G 2811

(SEQ ID NO:3)

FIG. 4

METPSQRRAT RSGAQASSTP LSPTRITRLQ EKEDLQELND RLAVYIDRVR SLETENAGLR 60
LRITESEEVV SREVSGIKAA YEAELGDARK TLDSVAKERA RLQLELSKVR EEFKELKARN 120
TKKEGDLIAA QARLKDLEAL LNSKEAALST ALSEKRTLEG ELHDLRGQVA KLEAALGEAK 180
KQLQDEMLRR VDAENRLQTM KEELDFQKNI YSEELRETKR RHETRLVEID NGKQREFESR 240
LADALQELRA QHEDQVEQYK KELEKTYSAK LDNARQSAER NSNLVGAAHE ELQQSRIRID 300
SLSAQLSQLQ KQLAAKEAKL RDLEDSLARE RDTSRRLLAE KEREMAEMRA RMQQQLDEYQ 360
ELLDIKLALD MEIHAYRKLL EGEEERLRLS PSPTSQRSRG RASSHSSQTQ GGGSVTKKRK 420
LESTESRSSF SQHARTSGRV AVEEVDEEGK FVRLRNKSNE DQSMGNWQIK RQNGDDPLLT 480
YRFPPKFTLK AGQVVTIWAA GAGATHSPPT DLVWKAQNTW GCGNSLRTAL INSTGEEVAM 540
RKLVRSVTVV EDDEDEDGDD LLHHHH/DAIR SHSESASPSA LSSSPNNLSP TGWSQPKTPV 600
PAQRERAPVS GTQEKNKIRP RGQRDSSYYW EIEASEVMLS TRIGSGSFGT VYKGKWHGDV 660
AVKILKVVDP TPEQFQAFRN EVAVLRKTRH VNILLFMGYM TKDNLAIVTQ WCEGSSLYKH 720
LHVQETKFQM FQLIDIARQT AQGMDYLHAK NIIHRDMKSN NIFLHEGLTV KIGDFGLATV 780
KSRWSGSQQV EQPTGSVLWM APEVIRMQDN NPFSFQSDVY SYGIVLYELM TGELPYSHIN 840
NRDQIIFMVG RGYASPDLSK LYKNCPKAMK RLVADCVKKV KEERPLFPQI LSSIELLQHS 900
LPKINRSASE PSLHRAAHTE DINACTLTTS PRLPVF (SEQ ID NO:4)

FIG. 5A

ATGTCGGCAG CCAAGGAGAA CCCGTGCAGG AAATTCCAGG CCAACATCTT CAACAAGAGC 60
AAGTGTCAGA ACTGCTTCAA GCCCCGCGAG TCGCATCTGC TCAACGACGA GGACCTGACG 120
CAGGCAAAAC CCATTTATGG CGGTTGGCTG CTCCTGGCTC CAGATGGGAC CGACTTTGAC 180
AACCCAGTGC ACCGGTCTCG GAAATGGCAG CGACGGTTCT TCATCCTTTA CGAGCACGGC 240
CTCTTGCGCT ACGCCCTGGA TGAGATGCCC ACGACCCTTC CTCAGGGCAC CATCAACATG 300
AACCAGTGCA CAGATGTGGT GGATGGGGAG GGCCGCACGG GCCAGAAGTT CTCCCTGTGT 360
ATTCTGACGC CTGAGAAGGA GCATTTCATC CGGGCGGAGA CCAAGGAGAT CGTCAGTGGG 420
TGGCTGGAGA TGCTCATGGT CTATCCCCGG ACCAACAAGC AGAATCAGAA GAAGAAACGG 480
AAAGTGGAGC CCCCCACACC ACAGGAGCCT GGGCCTGCCA AGGTGGCTGT TACCAGCAGC 540
AGCAGCAGCA GCAGCAGCAG CAGCAGCATC CCCAGTGCTG AGAAAGTCCC CACCACCAAG 600
TCCACACTCT GGCAGGAAGA AATGAGGACC AAGGACCAGC CAGATGGCAG CAGCCTGAGT 660
CCAGCTCAGA GTCCCAGCCA GAGCCAGCCT CCTGCTGCCA GCTCCCTGCG GGAACCTGGG 720
CTAGAGAGCA AAGAAGAGGA GAGCGCCATG AGTAGCGACC GCATGGACTG TGGCCGCAAA 780
GTCCGGGTGG AGAGCGGCTA CTTCTCTCTG GAGAAGACCA AACAGGACTT GAAGGCTGAA 840
GAACAGCAGC TGCCCCCGCC GCTCTCCCCT CCCAGCCCCA GCACCCCCAA CCACAGGAGG 900
TCCCAGGTGA TTGAAAAGTT TGAGGCCTTG GACATTGAGA AGGCAGAGCA CATGGAGACC 960
AATGCAGTGG GGCCCTCACC ATCCAGCGAC ACACGCCAGG GCCGCAGCGA GAAGAGGGCG 1020
TTCCCTAGGA AGCGGGACTT CACCAATGAA GCCCCCCCAG CTCCTCTCCC AGACGCCTCG 1080
GCTTCCCCCC TGTCTCCACA CCGAAGAGCC AAGTCACTGG ACAGGAGGTC CACGGAGCCC 1140
TCCGTGACGC CCGACCTGCT GAATTTCAAG AAAGGCTGGC TGACTAAGCA GTATGAGGAC 1200
GGCCAGTGGA AGAAACACTG GTTTGTCCTC GCCGATCAAA GCCTGAGATA CTACAGGGAT 1260
TCAGTGGCTG AGGAGGCAGC CGACTTGGAT GGAGAAATTG ACTTGTCCGC ATGTTACGAT 1320
GTCACAGAGT ATCCAGTTCA GAGAAACTAT GGCTTCCAGA TACATACAAA GGAGGGCGAG 1380
TTTACCCTGT CGGCCATGAC ATCTGGGATT CGGCGGAACT GGATCCAGAC CATCATGAAG 1440
CACGTGCACC CGACCACTGC CCCGGATGTG ACCAGCTCGT TGCCAGAGGA AAAAAACAAG 1500
AGCAGCTGCT CTTTTGAGAC CTGCCCGAGG CCTACTGAGA AGCAAGAGGC AGAGCTGGGG 1560
GAGCCGGACC CTGAGCAGAA GAGGAGCCGC GCACGGGAGC GGAGGCGAGA GGGCCGCTCC 1620
AAGACCTTTG ACTGGGCTGA GTTCCGTCCC ATCCAGCAGG CCCTGGCTCA GGAGCGGGTG 1680
GGCGGCGTGG GGCCTGCTGA CACCCACGAG CCCCTGCGCC CTGAGGCGGA GCCTGGGGAG 1740
CTGGAGCGGG AGCGTGCACG GAGGCGGGAG GAGCGCCGCA AGCGCTTCGG GATGCTCGAC 1800
GCCACAGACG GGCCAGGCAC TGAGGATGCA GCCCTGCGCA TGGAGGTGGA CCGGAGCCCA 1860
GGGCTGCCTA TGAGCGACCT CAAAACGCAT AACGTCCACG TGGAGATTGA GCAGCGGTGG 1920
CATCAGGTGG AGACCACACC TCTCCGGGAA GAGAAGCAGG TGCCCATCGC CCCCGTCCAC 1980
CTGTCTTCTG AAGATGGGGG TGACCGGCTC TCCACACACG AGCTGACCTC TCTGCTCGAG 2040
AAGGAGCTGG AGCAGAGCCA GAAGGAGGCC TCAGACCTTC TGGAGCAGAA CCGGCTCCTG 2100
CAGGACCAGC TGAGGGTGGC CCTGGGCCGG GAGCAGAGCG CCCGTGAGGG CTACGTGCTG 2160
CAGGCCACGT GCGAGCGAGG GTTTGCAGCA ATGGAAGAAA CGCACCAGAA GAAGATTGAA 2220
GATCTCCAGA GGCAGCACCA GCGGGAGCTA GAGAAACTTC GAGAAGAGAA AGACCGCCTC 2280
CTAGCCGAGG AGACAGCGGC CACCATCTCA GCCATCGAAG CCATGAAGAA CGCCCACCGG 2340
GAGGAAATGG AGCGGGAGCT GGAGAAGAGC CAGCGGTCCC AGATCAGCAG CGTCAACTCG 2400
GATGTTGAGG CCCTGCGGCG CCAGTACCTG GAGGAGCTGC AGTCGGTGCA GCGGGAACTG 2460
GAGGTCCTCT CGGAGCAGTA CTCGCAGAAG TGCCTGGAGA ATGCCCATCT GGCCCAGGCG 2520
CTGGAGGCCG AGCGGCAGGC CCTGCGGCAG TGCCAGCGTG AGAACCAGGA GCTCAATGCC 2580
CACAACCAGG AGCTGAACAA CCGCCTGGCT GCAGAGATCA CACGGTTGCG GACGCTGCTG 2640
ACTGGGGACG GCGGTGGGGA GGCCACTGGG TCACCCCTTG CACAGGGCAA GGATGCCTAT 2700
GAACTAGAGG TCTTATTGCG GGTAAAGGAA TCGGAAATAC AGTACCTGAA ACAGGAGATT 2760
AGCTCCCTCA AGGATGAGCT GCAGACGGCA CTGCGGGACA AGAAGTACGC AAGTGACAAG 2820
TACAAAGACA TCTACACAGA GCTCAGCATC GCGAAGGCTA AGGCTGACTG TGACATCAGC 2880
AGGTTGAAGG AGCAGCTCAA GGCTGCAACG GAAGCACTGG GGGAGAAGTC CCCTGACAGT 2940
GCCACGGTGT CCGGATATGA TATAATGAAA TCTAAAAGCA ACCCTGACTT CTTGAAGAAA 3000
GACAGATCCT GTGTCACCCG GCAACTCAGA AACATCAGGT CCAAG/GATGC AATTCGAAGT 3060

FIG. 5B

```
CACAGCGAAT CAGCCTCACC TTCAGCCCTG TCCAGTAGCC CCAACAATCT GAGCCCAACA  3120
GGCTGGTCAC AGCCGAAAAC CCCCGTGCCA GCACAAAGAG AGCGGGCACC AGTATCTGGG  3180
ACCCAGGAGA AAAACAAAAT TAGGCCTCGT GGACAGAGAG ATTCAAGCTA TTATTGGGAA  3240
ATAGAAGCCA GTGAAGTGAT GCTGTCCACT CGGATTGGGT CAGGCTCTTT TGGAACTGTT  3300
TATAAGGGTA AATGGCACGG AGATGTTGCA GTAAAGATCC TAAAGGTTGT CGACCCAACC  3360
CCAGAGCAAT TCCAGGCCTT CAGGAATGAG GTGGCTGTTC TGCGCAAAAC ACGGCATGTG  3420
AACATTCTGC TTTTCATGGG GTACATGACA AAGGACAACC TGGCAATTGT GACCCAGTGG  3480
TGCGAGGGCA GCAGCCTCTA CAAACACCTG CATGTCCAGG AGACCAAGTT TCAGATGTTC  3540
CAGCTAATTG ACATTGCCCG GCAGACGGCT CAGGGAATGG ACTATTTGCA TGCAAAGAAC  3600
ATCATCCATA GAGACATGAA ATCCAACAAT ATATTTCTCC ATGAAGGCTT AACAGTGAAA  3660
ATTGGAGATT TTGGTTTGGC AACAGTAAAG TCACGCTGGA GTGGTTCTCA GCAGGTTGAA  3720
CAACCTACTG GCTCTGTCCT CTGGATGGCC CCAGAGGTGA TCCGAATGCA GGATAACAAC  3780
CCATTCAGTT TCCAGTCGGA TGTCTACTCC TATGGCATCG TATTGTATGA ACTGATGACG  3840
GGGGAGCTTC CTTATTCTCA CATCAACAAC CGAGATCAGA TCATCTTCAT GGTGGGCCGA  3900
GGATATGCCT CCCCAGATCT TAGTAAGCTA TATAAGAACT GCCCCAAAGC AATGAAGAGG  3960
CTGGTAGCTG ACTGTGTGAA GAAAGTAAAG GAAGAGAGGC CTCTTTTTCC CCAGATCCTG  4020
TCTTCCATTG AGCTGCTCCA ACACTCTCTA CCGAAGATCA ACCGGAGCGC TTCCGAGCCA  4080
TCCTTGCATC GGGCAGCCCA CACTGAGGAT ATCAATGCTT GCACGCTGAC CACGTCCCCG  4140
AGGCTGCCTG TCTTCTAG
```

(SEQ ID NO:5)

FIG. 6

MSAAKENPCR KFQANIFNKS KCQNCFKPRE SHLLNDEDLT QAKPIYGGWL LLAPDGTDFD 60
NPVHRSRKWQ RRFFILYEHG LLRYALDEMP TTLPQGTINM NQCTDVVDGE GRTGQKFSLC 120
ILTPEKEHFI RAETKEIVSG WLEMLMVYPR TNKQNQKKKR KVEPPTPQEP GPAKVAVTSS 180
SSSSSSSSSI PSAEKVPTTK STLWQEEMRT KDQPDGSSLS PAQSPSQSQP PAASSLREPG 240
LESKEEESAM SSDRMDCGRK VRVESGYFSL EKTKQDLKAE EQQLPPPLSP PSPSTPNHRR 300
SQVIEKFEAL DIEKAEHMET NAVGPSPSSD TRQGRSEKRA FPRKRDFTNE APPAPLPDAS 360
ASPLSPHRRA KSLDRRSTEP SVTPDLLNFK KGWLTKQYED GQWKKHWFVL ADQSLRYYRD 420
SVAEEAADLD GEIDLSACYD VTEYPVQRNY GFQIHTKEGE FTLSAMTSGI RRNWIQTIMK 480
HVHPTTAPDV TSSLPEEKNK SSCSFETCPR PTEKQEAELG EPDPEQKRSR ARERRREGRS 540
KTFDWAEFRP IQQALAQERV GGVGPADTHE PLRPEAEPGE LERERARRRE ERRKRFGMLD 600
ATDGPGTEDA ALRMEVDRSP GLPMSDLKTH NVHVEIEQRW HQVETTPLRE EKQVPIAPVH 660
LSSEDGGDRL STHELTSLLE KELEQSQKEA SDLLEQNRLL QDQLRVALGR EQSAREGYVL 720
QATCERGFAA MEETHQKKIE DLQRQHQREL EKLREEKDRL LAEETAATIS AIEAMKNAHR 780
EEMERELEKS QRSQISSVNS DVEALRRQYL EELQSVQREL EVLSEQYSQK CLENAHLAQA 840
LEAERQALRQ CQRENQELNA HNQELNNRLA AEITRLRTLL TGDGGGEATG SPLAQGKDAY 900
ELEVLLRVKE SEIQYLKQEI SSLKDELQTA LRDKKYASDK YKDIYTELSI AKAKADCDIS 960
RLKEQLKAAT EALGEKSPDS ATVSGYDIMK SKSNPDFLKK DRSCVTRQLR NIRSK/DAIRS 1020
HSESASPSAL SSSPNNLSPT GWSQPKTPVP AQRERAPVSG TQEKNKIRPR GQRDSSYYWE 1080
IEASEVMLST RIGSGSFGTV YKGKWHGDVA VKILKVVDPT PEQFQAFRNE VAVLRKTRHV 1140
NILLFMGYMT KDNLAIVTQW CEGSSLYKHL HVQETKFQMF QLIDIARQTA QGMDYLHAKN 1200
IIHRDMKSNN IFLHEGLTVK IGDFGLATVK SRWSGSQQVE QPTGSVLWMA PEVIRMQDNN 1260
PFSFQSDVYS YGIVLYELMT GELPYSHINN RDQIIFMVGR GYASPDLSKL YKNCPKAMKR 1320
LVADCVKKVK EERPLFPQIL SSIELLQHSL PKINRSASEP SLHRAAHTED INACTLTTSP 1380
RLPVF (SEQ ID NO:6)

FIG. 7

ATGTCCCCTT GTCCTGAAGA AGCAGCTATG AGAAGAGAGG TGGTGAAACG GATCGAAACT 60
GTGGTGAAAG ACCTTTGGCC GACGGCTGAT GTACAGATAT TTGGCAGCTT TAGTACAGGT 120
CTTTATCTTC CAACTAGCGA CATAGACCTG GTGGTCTTCG GGAAATGGGA GCGTCCTCCT 180
TTACAGCTGC TGGAGCAAGC CCTGCGGAAG CACAACGTGG CTGAGCCGTG TTCCATCAAA 240
GTCCTTGACA AGGCTACGGT ACCAATAATA AAGCTCACAG ATCAGGAGAC TGAAGTGAAA 300
GTTGACATCA GCTTTAACAT GGAGACGGGC GTCCGGGCAG CGGAGTTCAT CAAGAATTAC 360
ATGAAGAAAT ATTCATTGCT GCCTTACTTG ATTTTAGTAT TGAAACAGTT CCTTCTGCAG 420
AGGGACCTGA ATGAAGTTTT TACAGGTGGA ATTAGCTCAT ACAGCCTAAT TTTAATGGCC 480
ATTAGCTTTC TACAGTTGCA TCCAAGAATT GATGCCCGGA GAGCTGATGA AAACCTTGGA 540
ATGCTTCTTG TAGAATTTTT TGAACTCTAT GGGAGAAATT TTAATTACTT GAAAACCGGT 600
ATTAGAATCA AAGAAGGAGG TGCCTATATC GCCAAAGAGG AGATCATGAA AGCCATGACC 660
AGCGGGTACA GACCGTCGAT GCTGTGCATT GAGGACCCCC TGCTGCCAGG GAATGACGTT 720
GGCCGGAGCT CCTATGGCGC CATGCAGGTG AAGCAGGTCT TCGATTATGC CTACATAGTG 780
CTCAGCCATG CTGTGTCACC GCTGGCCAGG TCCTATCCAA ACAGAGACGC CGAAAGTACT 840
TTAGGAAGAA TCATCAAAGT AACTCAGGAG GTGATTGACT ACCGGAGGTG GATCAAAGAG 900
AAGTGGGGCA GCAAAGCCCA CCCGTCGCCA GGCATGGACA GCAGGATCAA GATCAAAGAG 960
CGAATAGCCA CATGCAATGG GGAGCAGACG CAGAACCGAG AGCCCGAGTC TCCCTATGGC 1020
CAGCGCTTGA CTTTGTCGCT GTCCAGCCCC CAGCTCCTGT CTTCAGGCTC CTCGGCCTCT 1080
TCTGTGTCTT CACTTTCTGG GAGTGACGTT GATTCAGACA CACCGCCCTG CACAACGCCC 1140
AGTGTTTACC AGTTCAGTCT GCAAGCGCCA GCTCCTCTCA TGGCCGGCTT ACCCACCGCC 1200
TTGCCAATGC CCAGTGGCAA ACCTCAGCCC ACCACTTCCA GAACACTGAT CATGACAACC 1260
AACAATCAG/A GGCCTCGTGG ACAGAGAGAT TCAAGCTATT ATTGGGAAAT AGAAGCCAGT 1320
GAAGTGATGC TGTCCACTCG GATTGGGTCA GGCTCTTTTG GAACTGTTTA TAAGGGTAAA 1380
TGGCACGGAG ATGTTGCAGT AAAGATCCTA AAGGTTGTCG ACCCAACCCC AGAGCAATTC 1440
CAGGCCTTCA GGAATGAGGT GGCTGTTCTG CGCAAAACAC GGCATGTGAA CATTCTGCTT 1500
TTCATGGGGT ACATGACAAA GGACAACCTG GCAATTGTGA CCCAGTGGTG CGAGGGCAGC 1560
AGCCTCTACA AACACCTGCA TGTCCAGGAG ACCAAGTTTC AGATGTTCCA GCTAATTGAC 1620
ATTGCCCGGC AGACGGCTCA GGGAATGGAC TATTTGCATG CAAAGAACAT CATCCATAGA 1680
GACATGAAAT CCAACAATAT ATTTCTCCAT GAAGGCTTAA CAGTGAAAAT TGGAGATTTT 1740
GGTTTGGCAA CAGTAAAGTC ACGCTGGAGT GGTTCTCAGC AGGTTGAACA ACCTACTGGC 1800
TCTGTCCTCT GGATGGCCCC AGAGGTGATC CGAATGCAGG ATAACAACCC ATTCAGTTTC 1860
CAGTCGGATG TCTACTCCTA TGGCATCGTA TTGTATGAAC TGATGACGGG GGAGCTTCCT 1920
TATTCTCACA TCAACAACCG AGATCAGATC ATCTTCATGG TGGGCCGAGG ATATGCCTCC 1980
CCAGATCTTA GTAAGCTATA TAAGAACTGC CCCAAAGCAA TGAAGAGGCT GGTAGCTGAC 2040
TGTGTGAAGA AAGTAAAGGA AGAGAGGCCT CTTTTTCCCC AGATCCTGTC TTCCATTGAG 2100
CTGCTCCAAC ACTCTCTACC GAAGATCAAC CGGAGCGCTT CCGAGCCATC CTTGCATCGG 2160
GCAGCCCACA CTGAGGATAT CAATGCTTGC ACGCTGACCA CGTCCCCGAG GCTGCCTGTC 2220
TTCTAG (SEQ ID NO:7)

FIG. 8

MSPCPEEAAM RREVVKRIET VVKDLWPTAD VQIFGSFSTG LYLPTSDIDL VVFGKWERPP 60

LQLLEQALRK HNVAEPCSIK VLDKATVPII KLTDQETEVK VDISFNMETG VRAAEFIKNY 120

MKKYSLLPYL ILVLKQFLLQ RDLNEVFTGG ISSYSLILMA ISFLQLHPRI DARRADENLG 180

MLLVEFFELY GRNFNYLKTG IRIKEGGAYI AKEEIMKAMT SGYRPSMLCI EDPLLPGNDV 240

GRSSYGAMQV KQVFDYAYIV LSHAVSPLAR SYPNRDAEST LGRIIKVTQE VIDYRRWIKE 300

KWGSKAHPSP GMDSRIKIKE RIATCNGEQT QNREPESPYG QRLTLSLSSP QLLSSGSSAS 360

SVSSLSGSDV DSDTPPCTTP SVYQFSLQAP APLMAGLPTA LPMPSGKPQP TTSRTLIMTT 420

NNQ/RPRGQRD SSYYWEIEAS EVMLSTRIGS GSFGTVYKGK WHGDVAVKIL KVVDPTPEQF 280

QAFRNEVAVL RKTRHVNILL FMGYMTKDNL AIVTQWCEGS SLYKHLHVQE TKFQMFQLID 540

IARQTAQGMD YLHAKNIIHR DMKSNNIFLH EGLTVKIGDF GLATVKSRWS GSQQVEQPTG 600

SVLWMAPEVI RMQDNNPFSF QSDVYSYGIV LYELMTGELP YSHINNRDQI IFMVGRGYAS 660

PDLSKLYKNC PKAMKRLVAD CVKKVKEERP LFPQILSSIE LLQHSLPKIN RSASEPSLHR 720

AAHTEDINAC TLTTSPRLPV F (SEQ ID NO:8)

FIG. 9

```
   1  ATGGCGGGGT GCAGGGGGTC TCTGTGCTGC TGCTGCAGGT GGTGCTGCTG    50
  51  CTGCGGTGAG CGTGAGACCC GCACCCCCGA GGAGCTGACC ATCCTTGGAG   100
 101  AAACACAGGA GGAGGAGGAT GAGATTCTTC CAAGGAAAGA CTATGAG/GAT  150
 151  GCAATTCGAA GTCACAGCGA ATCAGCCTCA CCTTCAGCCC TGTCCAGTAG   200
 201  CCCCAACAAT CTGAGCCCAA CAGGCTGGTC ACAGCCGAAA ACCCCCGTGC   250
 251  CAGCACAAAG AGAGCGGGCA CCAGTATCTG GGACCCAGGA GAAAAACAAA   300
 301  ATTAGGCCTC GTGGACAGAG AGATTCAAGC TATTATTGGG AAATAGAAGC   350
 351  CAGTGAAGTG ATGCTGTCCA CTCGGATTGG GTCAGGCTCT TTTGGAACTG   400
 401  TTTATAAGGG TAAATGGCAC GGAGATGTTG CAGTAAAGAT CCTAAAGGTT   450
 451  GTCGACCCAA CCCCAGAGCA ATTCCAGGCC TTCAGGAATG AGGTGGCTGT   500
 501  TCTGCGCAAA ACACGGCATG TGAACATTCT GCTTTTCATG GGGTACATGA   550
 551  CAAAGGACAA CCTGGCAATT GTGACCCAGT GGTGCGAGGG CAGCAGCCTC   600
 601  TACAAACACC TGCATGTCCA GGAGACCAAG TTTCAGATGT TCCAGCTAAT   650
 651  TGACATTGCC CGGCAGACGG CTCAGGGAAT GGACTATTTG CATGCAAAGA   700
 701  ACATCATCCA TAGAGACATG AAATCCAACA ATATATTTCT CCATGAAGGC   750
 751  TTAACAGTGA AAATTGGAGA TTTTGGTTTG GCAACAGTAA AGTCACGCTG   800
 801  GAGTGGTTCT CAGCAGGTTG AACAACCTAC TGGCTCTGTC CTCTGGATGG   850
 851  CCCCAGAGGT GATCCGAATG CAGGATAACA ACCCATTCAG TTTCCAGTCG   900
 901  GATGTCTACT CCTATGGCAT CGTATTGTAT GAACTGATGA CGGGGGAGCT   950
 951  TCCTTATTCT CACATCAACA ACCGAGATCA GATCATCTTC ATGGTGGGCC  1000
1001  GAGGATATGC CTCCCCAGAT CTTAGTAAGC TATATAAGAA CTGCCCCAAA  1050
1051  GCAATGAAGA GGCTGGTAGC TGACTGTGTG AAGAAAGTAA AGGAAGAGAG  1100
1101  GCCTCTTTTT CCCCAGATCC TGTCTTCCAT TGAGCTGCTC CAACACTCTC  1150
1151  TACCGAAGAT CAACCGGAGC GCTTCCGAGC CATCCTTGCA TCGGGCAGCC  1200
1201  CACACTGAGG ATATCAATGC TTGCACGCTG ACCACGTCCC CGAGGCTGCC  1250
1251  TGTCTTCTAG                                             1260
```

(SEQ ID NO:9)

FIG. 10

```
  1  MAGCRGSLCC CCRWCCCCGE RETRTPEELT ILGETQEEED EILPRKDYE/D  50
 51  AIRSHSESAS PSALSSSPNN LSPTGWSQPK TPVPAQRERA PVSGTQEKNK  100
101  IRPRGQRDSS YYWEIEASEV MLSTRIGSGS FGTVYKGKWH GDVAVKILKV  150
151  VDPTPEQFQA FRNEVAVLRK TRHVNILLFM GYMTKDNLAI VTQWCEGSSL  200
201  YKHLHVQETK FQMFQLIDIA RQTAQGMDYL HAKNIIHRDM KSNNIFLHEG  250
251  LTVKIGDFGL ATVKSRWSGS QQVEQPTGSV LWMAPEVIRM QDNNPFSFQS  300
301  DVYSYGIVLY ELMTGELPYS HINNRDQIIF MVGRGYASPD LSKLYKNCPK  350
351  AMKRLVADCV KKVKEERPLF PQILSSIELL QHSLPKINRS ASEPSLHRAA  400
401  HTEDINACTL TTSPRLPVF                                     419
```

(SEQ ID NO:10)

FIG. 11

```
   1 ATGGCATTGG TTTTTCAATT CGGGCAGCCC GTCAGGGCTC AGCCTCTGCC   50
  51 AGGACTCTGC CACGGCAAGC TCATTCGGAC AAACGCCTGT GATGTGTGCA  100
 101 ACAGCACCGA TCTTCCGGAA GTCGAGATCA TTAGCCTGCT GGAGGAGCAG  150
 151 CTGCCCCATT ATAAGTTAAG AGCCGACACC ATCTACGGTT ATGACCACGA  200
 201 CGACTGGCTC CATACACCTC TCATTTCTCC AGATGCCAAC ATTGACCTCA  250
 251 CAACCGAGCA AATTGAAGAG ACGTTAAAAT ACTTCCTTTT ATGTGCTGAA  300
 301 AGAGTTGGCC AGATGACTAA GACATATAAT GACATAGATG CTGTCACTCG  350
 351 GCTTCTTGAG GAGAAAGAGC GGGATTTAGA ATTGGCCGCT CGCATCGGCC  400
 401 AGTCGTTGTT GAAGAAGAAC AAGACCCTAA CCGAGAGGAA CGAGCTGCTG  450
 451 GAGGAGCAGG TGGAACACAT CAGGGAGGAG GTGTCTCAGC TCCGGCATGA  500
 501 GCTGTCCATG AAGGATGAGC TGCTTCAGTT CTACACCAGC GCTGCGGAGG  550
 551 AGAGTGAGCC CGAGTCCGTT TGCTCAACCC CGTTGAAGAG GAATGAGTCG  600
 601 TCCTCCTCAG TCCAGAATTA CTTTCATTTG GATTCTCTTC AAAAGAAGCT  650
 651 GAAAGACCTT GAAGAGGAGA ATGTTGTACT TCGATCCGAG GCCAGCCAGC  700
 701 TGAAGACAGA GACCATCACC TATGAGGAGA AGGAGCAGCA GCTGGTCAAT  750
 751 GACTGCGTGA AGGAGCTGAG GGATGCCAAT GTCCAGATTG CTAGTATCTC  800
 801 AGAGGAACTG GCCAAGAAGA CGGAAGATGC TGCCCGCCAG CAAGAGGAGA  850
 851 TCACACACCT GCTATCGCAA ATAGTTGATT TGCAGAAAAA GGCAAAAGCT  900
 901 TGCGCAGTGG AAAATGAAGA ACTTGTCCAG CATCTGGGGG CTGCTAAGGA  950
 951 TGCCCAGCGG CAGCTCACAG CCGAG/GATGCAATTCGAAGT CACAGCGAAT 1000
1001 CAGCCTCACC TTCAGCCCTG TCCAGTAGCC CCAACAATCT GAGCCCAACA 1050
1051 GGCTGGTCAC AGCCGAAAAC CCCCGTGCCA GCACAAAGAG AGCGGGCACC 1100
1101 AGTATCTGGG ACCCAGGAGA AAAACAAAAT TAGGCCTCGT GGACAGAGAG 1150
1151 ATTCAAGCTA TTATTGGGAA ATAGAAGCCA GTGAAGTGAT GCTGTCCACT 1200
1201 CGGATTGGGT CAGGCTCTTT TGGAACTGTT TATAAGGGTA AATGGCACGG 1250
1251 AGATGTTGCA GTAAAGATCC TAAAGGTTGT CGACCCAACC CCAGAGCAAT 1300
1301 TCCAGGCCTT CAGGAATGAG GTGGCTGTTC TGCGCAAAAC ACGGCATGTG 1350
1351 AACATTCTGC TTTTCATGGG GTACATGACA AAGGACAACC TGGCAATTGT 1400
1401 GACCCAGTGG TGCGAGGGCA GCAGCCTCTA CAAACACCTG CATGTCCAGG 1450
1451 AGACCAAGTT TCAGATGTTC CAGCTAATTG ACATTGCCCG GCAGACGGCT 1500
1501 CAGGGAATGG ACTATTTGCA TGCAAAGAAC ATCATCCATA GAGACATGAA 1550
1551 ATCCAACAAT ATATTTCTCC ATGAAGGCTT AACAGTGAAA ATTGGAGATT 1600
1601 TTGGTTTGGC AACAGTAAAG TCACGCTGGA GTGGTTCTCA GCAGGTTGAA 1650
1651 CAACCTACTG GCTCTGTCCT CTGGATGGCC CCAGAGGTGA TCCGAATGCA 1700
1701 GGATAACAAC CCATTCAGTT TCCAGTCGGA TGTCTACTCC TATGGCATCG 1750
1751 TATTGTATGA ACTGATGACG GGGGAGCTTC CTTATTCTCA CATCAACAAC 1800
1801 CGAGATCAGA TCATCTTCAT GGTGGGCCGA GGATATGCCT CCCCAGATCT 1850
1851 TAGTAAGCTA TATAAGAACT GCCCCAAAGC AATGAAGAGG CTGGTAGCTG 1900
1901 ACTGTGTGAA GAAAGTAAAG GAAGAGAGGC CTCTTTTTCC CCAGATCCTG 1950
1951 TCTTCCATTG AGCTGCTCCA ACACTCTCTA CCGAAGATCA ACCGGAGCGC 2000
2001 TTCCGAGCCA TCCTTGCATC GGGCAGCCCA CACTGAGGAT ATCAATGCTT 2050
2051 GCACGCTGAC CACGTCCCCG AGGCTGCCTG TCTTCTAG             2088
```

(SEQ ID NO:11)

FIG. 12

```
  1  MALVFQFGQP VRAQPLPGLC HGKLIRTNAC DVCNSTDLPE VEIISLLEEQ   50
 51  LPHYKLRADT IYGYDHDDWL HTPLISPDAN IDLTTEQIEE TLKYFLLCAE  100
101  RVGQMTKTYN DIDAVTRLLE EKERDLELAA RIGQSLLKKN KTLTERNELL  150
151  EEQVEHIREE VSQLRHELSM KDELLQFYTS AAEESEPESV CSTPLKRNES  200
201  SSSVQNYFHL DSLQKKLKDL EEENVVLRSE ASQLKTETIT YEEKEQQLVN  250
251  DCVKELRDAN VQIASISEEL AKKTEDAARQ QEEITHLLSQ IVDLQKKAKA  300
301  CAVENEELVQ HLGAAKDAQR QLTAE/DAIRSHSESASPSAL SSSPNNLSPT  350
351  GWSQPKTPVP AQRERAPVSG TQEKNKIRPR GQRDSSYYWE IEASEVMLST  400
401  RIGSGSFGTV YKGKWHGDVA VKILKVVDPT PEQFQAFRNE VAVLRKTRHV  450
451  NILLFMGYMT KDNLAIVTQW CEGSSLYKHL HVQETKFQMF QLIDIARQTA  500
501  QGMDYLHAKN IIHRDMKSNN IFLHEGLTVK IGDFGLATVK SRWSGSQQVE  550
551  QPTGSVLWMA PEVIRMQDNN PFSFQSDVYS YGIVLYELMT GELPYSHINN  600
601  RDQIIFMVGR GYASPDLSKL YKNCPKAMKR LVADCVKKVK EERPLFPQIL  650
651  SSIELLQHSL PKINRSASEP SLHRAAHTED INACTLTTSP RLPVF        695
```

(SEQ ID NO:12)

SEQUENCE LISTING

```
<160> NUMBER OF SEQ ID NOS: 12

<210> SEQ ID NO 1
<211> LENGTH: 1983
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

atggcctcgg aggcgccgtc cccgccgcgg tcgccgccgc cgcccacctc ccccgagcct     60

gagctggccc agctaaggcg gaaggtggag aagttggaac gtgaactgcg gagctgcaag    120

cggcaggtgc gggagatcga gaagctgctg catcacacag aacggctgta ccagaacgca    180

gaaagcaaca accaggagct ccgcacgcag gtggaagaac tcagtaaaat actccaacgt    240

gggagaaatg aagataataa aaagtctgat gtagaagtac aaacagagaa ccatgctcct    300

tggtcaatct cagattattt ttatcagacg tactacaatg acgttagtct tccaaataaa    360

gtgactgaac tgtcagatca acaagatcaa gctatcgaaa cttctatttt gaattctaaa    420

gaccatttac aagtagaaaa tgatgcttac cctggtaccg atagaacaga aaatgttaaa    480

tatagacaag tggaccattt tgcctcaaat tcacaggagc cagcatctgc attagcaaca    540

gaagatacct ccttagaagg ctcatcatta gctgaaagtt tgagagctgc agcagaagcg    600

gctgtatcac agactggatt tagttatgat gaaaatactg gactgtattt tgaccacagc    660

actggtttct attatgattc tgaaaatcaa ctctattatg atccttccac tggaatttat    720

tactattgtg atgtggaaag tggtcgttat cagtttcatt ctcgagtaga tttgcaacct    780

tatccgactt ctagcacaaa acaaagtaaa gataaaaaat tgaagaagaa aagaaaagat    840

ccagattctt ctgcaacaaa tgaggaaaag gatgcaattc gaagtcacag cgaatcagcc    900

tcaccttcag ccctgtccag tagccccaac aatctgagcc caacaggctg gtcacagccg    960

aaaacccccg tgccagcaca aagagagcgg gcaccagtat ctgggaccca ggagaaaaac   1020
```

-continued

```
aaaattaggc ctcgtggaca gagagattca agctattatt gggaaataga agccagtgaa   1080

gtgatgctgt ccactcggat tgggtcaggc tcttttggaa ctgtttataa gggtaaatgg   1140

cacggagatg ttgcagtaaa gatcctaaag gttgtcgacc caaccccaga gcaattccag   1200

gccttcagga atgaggtggc tgttctgcgc aaaacacggc atgtgaacat tctgcttttc   1260

atggggtaca tgacaaagga caacctggca attgtgaccc agtggtgcga gggcagcagc   1320

ctctacaaac acctgcatgt ccaggagacc aagtttcaga tgttccagct aattgacatt   1380

gcccggcaga cggctcaggg aatggactat ttgcatgcaa agaacatcat ccatagagac   1440

atgaaatcca acaatatatt tctccatgaa ggcttaacag tgaaaattgg agattttggt   1500

ttggcaacag taaagtcacg ctggagtggt tctcagcagg ttgaacaacc tactggctct   1560

gtcctctgga tggccccaga ggtgatccga atgcaggata acaacccatt cagtttccag   1620

tcggatgtct actcctatgg catcgtattg tatgaactga tgacggggga gcttccttat   1680

tctcacatca acaaccgaga tcagatcatc ttcatggtgg gccgaggata tgcctcccca   1740

gatcttagta agctatataa gaactgcccc aaagcaatga agaggctggt agctgactgt   1800

gtgaagaaag taaaggaaga gaggcctctt tttccccaga tcctgtcttc cattgagctg   1860

ctccaacact ctctaccgaa gatcaaccgg agcgcttccg agccatcctt gcatcgggca   1920

gcccacactg aggatatcaa tgcttgcacg ctgaccacgt ccccgaggct gcctgtcttc   1980

tag                                                                 1983
```

```
<210> SEQ ID NO 2
<211> LENGTH: 660
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Ala Ser Glu Ala Pro Ser Pro Pro Arg Ser Pro Pro Pro Pro Thr
1               5                   10                  15

Ser Pro Glu Pro Glu Leu Ala Gln Leu Arg Arg Lys Val Glu Lys Leu
            20                  25                  30

Glu Arg Glu Leu Arg Ser Cys Lys Arg Gln Val Arg Glu Ile Glu Lys
        35                  40                  45

Leu Leu His His Thr Glu Arg Leu Tyr Gln Asn Ala Glu Ser Asn Asn
    50                  55                  60

Gln Glu Leu Arg Thr Gln Val Glu Glu Leu Ser Lys Ile Leu Gln Arg
65                  70                  75                  80

Gly Arg Asn Glu Asp Asn Lys Lys Ser Asp Val Glu Val Gln Thr Glu
                85                  90                  95

Asn His Ala Pro Trp Ser Ile Ser Asp Tyr Phe Tyr Gln Thr Tyr Tyr
            100                 105                 110

Asn Asp Val Ser Leu Pro Asn Lys Val Thr Glu Leu Ser Asp Gln Gln
        115                 120                 125

Asp Gln Ala Ile Glu Thr Ser Ile Leu Asn Ser Lys Asp His Leu Gln
    130                 135                 140

Val Glu Asn Asp Ala Tyr Pro Gly Thr Asp Arg Thr Glu Asn Val Lys
145                 150                 155                 160

Tyr Arg Gln Val Asp His Phe Ala Ser Asn Ser Gln Glu Pro Ala Ser
                165                 170                 175
```

-continued

```
Ala Leu Ala Thr Glu Asp Thr Ser Leu Glu Gly Ser Ser Leu Ala Glu
            180                 185                 190

Ser Leu Arg Ala Ala Ala Glu Ala Ala Val Ser Gln Thr Gly Phe Ser
        195                 200                 205

Tyr Asp Glu Asn Thr Gly Leu Tyr Phe Asp His Ser Thr Gly Phe Tyr
    210                 215                 220

Tyr Asp Ser Glu Asn Gln Leu Tyr Tyr Asp Pro Ser Thr Gly Ile Tyr
225                 230                 235                 240

Tyr Tyr Cys Asp Val Glu Ser Gly Arg Tyr Gln Phe His Ser Arg Val
                245                 250                 255

Asp Leu Gln Pro Tyr Pro Thr Ser Ser Thr Lys Gln Ser Lys Asp Lys
            260                 265                 270

Lys Leu Lys Lys Lys Arg Lys Asp Pro Asp Ser Ser Ala Thr Asn Glu
        275                 280                 285

Glu Lys Asp Ala Ile Arg Ser His Ser Glu Ser Ala Ser Pro Ser Ala
    290                 295                 300

Leu Ser Ser Ser Pro Asn Asn Leu Ser Pro Thr Gly Trp Ser Gln Pro
305                 310                 315                 320

Lys Thr Pro Val Pro Ala Gln Arg Glu Arg Ala Pro Val Ser Gly Thr
                325                 330                 335

Gln Glu Lys Asn Lys Ile Arg Pro Arg Gly Gln Arg Asp Ser Ser Tyr
            340                 345                 350

Tyr Trp Glu Ile Glu Ala Ser Glu Val Met Leu Ser Thr Arg Ile Gly
        355                 360                 365

Ser Gly Ser Phe Gly Thr Val Tyr Lys Gly Lys Trp His Gly Asp Val
    370                 375                 380

Ala Val Lys Ile Leu Lys Val Val Asp Pro Thr Pro Glu Gln Phe Gln
385                 390                 395                 400

Ala Phe Arg Asn Glu Val Ala Val Leu Arg Lys Thr Arg His Val Asn
                405                 410                 415

Ile Leu Leu Phe Met Gly Tyr Met Thr Lys Asp Asn Leu Ala Ile Val
            420                 425                 430

Thr Gln Trp Cys Glu Gly Ser Ser Leu Tyr Lys His Leu His Val Gln
        435                 440                 445

Glu Thr Lys Phe Gln Met Phe Gln Leu Ile Asp Ile Ala Arg Gln Thr
    450                 455                 460

Ala Gln Gly Met Asp Tyr Leu His Ala Lys Asn Ile Ile His Arg Asp
465                 470                 475                 480

Met Lys Ser Asn Asn Ile Phe Leu His Glu Gly Leu Thr Val Lys Ile
                485                 490                 495

Gly Asp Phe Gly Leu Ala Thr Val Lys Ser Arg Trp Ser Gly Ser Gln
            500                 505                 510

Gln Val Glu Gln Pro Thr Gly Ser Val Leu Trp Met Ala Pro Glu Val
        515                 520                 525

Ile Arg Met Gln Asp Asn Asn Pro Phe Ser Phe Gln Ser Asp Val Tyr
    530                 535                 540

Ser Tyr Gly Ile Val Leu Tyr Glu Leu Met Thr Gly Glu Leu Pro Tyr
545                 550                 555                 560

Ser His Ile Asn Asn Arg Asp Gln Ile Ile Phe Met Val Gly Arg Gly
                565                 570                 575

Tyr Ala Ser Pro Asp Leu Ser Lys Leu Tyr Lys Asn Cys Pro Lys Ala
            580                 585                 590

Met Lys Arg Leu Val Ala Asp Cys Val Lys Lys Val Lys Glu Glu Arg
```

-continued

```
        595                 600                 605

Pro Leu Phe Pro Gln Ile Leu Ser Ser Ile Glu Leu Leu Gln His Ser
    610                 615                 620

Leu Pro Lys Ile Asn Arg Ser Ala Ser Glu Pro Ser Leu His Arg Ala
625                 630                 635                 640

Ala His Thr Glu Asp Ile Asn Ala Cys Thr Leu Thr Thr Ser Pro Arg
                645                 650                 655

Leu Pro Val Phe
            660


<210> SEQ ID NO 3
<211> LENGTH: 2811
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3

atggagaccc cgtcccagcg gcgcgccacc cgcagcgggg cgcaggccag ctccactccg     60

ctgtcgccca cccgcatcac ccggctgcag gagaaggagg acctgcagga gctcaatgat    120

cgcttggcgg tctacatcga ccgtgtgcgc tcgctggaaa cggagaacgc agggctgcgc    180

cttcgcatca ccgagtctga agaggtggtc agccgcgagg tgtccggcat caaggccgcc    240

tacgaggccg agctcgggga tgcccgcaag acccttgact cagtagccaa ggagcgcgcc    300

cgcctgcagc tggagctgag caaagtgcgt gaggagttta aggagctgaa agcgcgcaat    360

accaagaagg agggtgacct gatagctgct caggctcggc tgaaggacct ggaggctctg    420

ctgaactcca aggaggccgc actgagcact gctctcagtg agaagcgcac gctggagggc    480

gagctgcatg atctgcgggg ccaggtggcc aagcttgagg cagccctagg tgaggccaag    540

aagcaacttc aggatgagat gctgcggcgg gtggatgctg agaacaggct gcagaccatg    600

aaggaggaac tggacttcca gaagaacatc tacagtgagg agctgcgtga gaccaagcgc    660

cgtcatgaga cccgactggt ggagattgac aatgggaagc agcgtgagtt tgagagccgg    720

ctggcggatg cgctgcagga actgcgggcc cagcatgagg accaggtgga gcagtataag    780

aaggagctgg agaagactta ttctgccaag ctggacaatg ccaggcagtc tgctgagagg    840

aacagcaacc tggtgggggc tgcccacgag gagctgcagc agtcgcgcat ccgcatcgac    900

agcctctctg cccagctcag ccagctccag aagcagctgg cagccaagga ggcgaagctt    960

cgagacctgg aggactcact ggcccgtgag cgggacacca gccggcggct gctggcggaa   1020

aaggagcggg agatggccga gatgcgggca aggatgcagc agcagctgga cgagtaccag   1080

gagcttctgg acatcaagct ggccctggac atggagatcc acgcctaccg caagctcttg   1140

gagggcgagg aggagaggct acgcctgtcc cccagcccta cctcgcagcg cagccgtggc   1200

cgtgcttcct ctcactcatc ccagacacag ggtgggggca gcgtcaccaa aaagcgcaaa   1260

ctggagtcca ctgagagccg cagcagcttc tcacagcacg cacgcactag cgggcgcgtg   1320

gccgtggagg aggtggatga ggagggcaag tttgtccggc tgcgcaacaa gtccaatgag   1380

gaccagtcca tgggcaattg gcagatcaag cgccagaatg gagatgatcc cttgctgact   1440

taccggttcc caccaaagtt caccctgaag gctgggcagg tggtgacgat ctgggctgca   1500

ggagctgggg ccacccacag ccccccctacc gacctggtgt ggaaggcaca gaacacctgg   1560

ggctgcggga acagcctgcg tacggctctc atcaactcca ctggggaaga agtggccatg   1620
```

cgcaagctgg tgcgctcagt gactgtggtt gaggacgacg aggatgagga tggagatgac 1680
ctgctccatc accaccacga tgcaattcga agtcacagcg aatcagcctc accttcagcc 1740
ctgtccagta gccccaacaa tctgagccca acaggctggt cacagccgaa aacccccgtg 1800
ccagcacaaa gagagcgggc accagtatct gggacccagg agaaaaacaa aattaggcct 1860
cgtggacaga gagattcaag ctattattgg gaaatagaag ccagtgaagt gatgctgtcc 1920
actcggattg ggtcaggctc ttttggaact gtttataagg gtaaatggca cggagatgtt 1980
gcagtaaaga tcctaaaggt tgtcgaccca accccagagc aattccaggc cttcaggaat 2040
gaggtggctg ttctgcgcaa aacacggcat gtgaacattc tgcttttcat ggggtacatg 2100
acaaaggaca acctggcaat tgtgacccag tggtgcgagg gcagcagcct ctacaaacac 2160
ctgcatgtcc aggagaccaa gtttcagatg ttccagctaa ttgacattgc ccggcagacg 2220
gctcagggaa tggactattt gcatgcaaag aacatcatcc atagagacat gaaatccaac 2280
aatatatttc tccatgaagg cttaacagtg aaaattggag attttggttt ggcaacagta 2340
aagtcacgct ggagtggttc tcagcaggtt gaacaaccta ctggctctgt cctctggatg 2400
gccccagagg tgatccgaat gcaggataac aacccattca gtttccagtc ggatgtctac 2460
tcctatggca tcgtattgta tgaactgatg acgggggagc ttccttattc tcacatcaac 2520
aaccgagatc agatcatctt catggtgggc cgaggatatg cctccccaga tcttagtaag 2580
ctatataaga actgccccaa agcaatgaag aggctggtag ctgactgtgt gaagaaagta 2640
aaggaagaga ggcctctttt tccccagatc ctgtcttcca ttgagctgct ccaacactct 2700
ctaccgaaga tcaaccggag cgcttccgag ccatccttgc atcgggcagc ccacactgag 2760
gatatcaatg cttgcacgct gaccacgtcc ccgaggctgc ctgtcttcta g 2811

<210> SEQ ID NO 4
<211> LENGTH: 936
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Met Glu Thr Pro Ser Gln Arg Arg Ala Thr Arg Ser Gly Ala Gln Ala
1 5 10 15

Ser Ser Thr Pro Leu Ser Pro Thr Arg Ile Thr Arg Leu Gln Glu Lys
20 25 30

Glu Asp Leu Gln Glu Leu Asn Asp Arg Leu Ala Val Tyr Ile Asp Arg
35 40 45

Val Arg Ser Leu Glu Thr Glu Asn Ala Gly Leu Arg Leu Arg Ile Thr
50 55 60

Glu Ser Glu Glu Val Val Ser Arg Glu Val Ser Gly Ile Lys Ala Ala
65 70 75 80

Tyr Glu Ala Glu Leu Gly Asp Ala Arg Lys Thr Leu Asp Ser Val Ala
85 90 95

Lys Glu Arg Ala Arg Leu Gln Leu Glu Leu Ser Lys Val Arg Glu Glu
100 105 110

Phe Lys Glu Leu Lys Ala Arg Asn Thr Lys Lys Glu Gly Asp Leu Ile
115 120 125

Ala Ala Gln Ala Arg Leu Lys Asp Leu Glu Ala Leu Leu Asn Ser Lys
130 135 140

-continued

```
Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560
```

-continued

```
Leu Leu His His His His Asp Ala Ile Arg Ser His Ser Glu Ser Ala
                565                 570                 575

Ser Pro Ser Ala Leu Ser Ser Ser Pro Asn Asn Leu Ser Pro Thr Gly
            580                 585                 590

Trp Ser Gln Pro Lys Thr Pro Val Pro Ala Gln Arg Glu Arg Ala Pro
        595                 600                 605

Val Ser Gly Thr Gln Glu Lys Asn Lys Ile Arg Pro Arg Gly Gln Arg
    610                 615                 620

Asp Ser Ser Tyr Tyr Trp Glu Ile Glu Ala Ser Glu Val Met Leu Ser
625                 630                 635                 640

Thr Arg Ile Gly Ser Gly Ser Phe Gly Thr Val Tyr Lys Gly Lys Trp
                645                 650                 655

His Gly Asp Val Ala Val Lys Ile Leu Lys Val Val Asp Pro Thr Pro
            660                 665                 670

Glu Gln Phe Gln Ala Phe Arg Asn Glu Val Ala Val Leu Arg Lys Thr
        675                 680                 685

Arg His Val Asn Ile Leu Leu Phe Met Gly Tyr Met Thr Lys Asp Asn
    690                 695                 700

Leu Ala Ile Val Thr Gln Trp Cys Glu Gly Ser Ser Leu Tyr Lys His
705                 710                 715                 720

Leu His Val Gln Glu Thr Lys Phe Gln Met Phe Gln Leu Ile Asp Ile
                725                 730                 735

Ala Arg Gln Thr Ala Gln Gly Met Asp Tyr Leu His Ala Lys Asn Ile
            740                 745                 750

Ile His Arg Asp Met Lys Ser Asn Asn Ile Phe Leu His Glu Gly Leu
        755                 760                 765

Thr Val Lys Ile Gly Asp Phe Gly Leu Ala Thr Val Lys Ser Arg Trp
    770                 775                 780

Ser Gly Ser Gln Gln Val Glu Gln Pro Thr Gly Ser Val Leu Trp Met
785                 790                 795                 800

Ala Pro Glu Val Ile Arg Met Gln Asp Asn Asn Pro Phe Ser Phe Gln
                805                 810                 815

Ser Asp Val Tyr Ser Tyr Gly Ile Val Leu Tyr Glu Leu Met Thr Gly
            820                 825                 830

Glu Leu Pro Tyr Ser His Ile Asn Asn Arg Asp Gln Ile Ile Phe Met
        835                 840                 845

Val Gly Arg Gly Tyr Ala Ser Pro Asp Leu Ser Lys Leu Tyr Lys Asn
    850                 855                 860

Cys Pro Lys Ala Met Lys Arg Leu Val Ala Asp Cys Val Lys Lys Val
865                 870                 875                 880

Lys Glu Glu Arg Pro Leu Phe Pro Gln Ile Leu Ser Ser Ile Glu Leu
                885                 890                 895

Leu Gln His Ser Leu Pro Lys Ile Asn Arg Ser Ala Ser Glu Pro Ser
            900                 905                 910

Leu His Arg Ala Ala His Thr Glu Asp Ile Asn Ala Cys Thr Leu Thr
        915                 920                 925

Thr Ser Pro Arg Leu Pro Val Phe
    930                 935
```

<210> SEQ ID NO 5
<211> LENGTH: 4159
<212> TYPE: DNA
<213> ORGANISM: Artificial Sequence
<220> FEATURE:
<221> NAME/KEY: source -continued
<223> OTHER INFORMATION: /note="Description of Artificial Sequence: Synthetic polynucleotide"

<400> SEQUENCE: 5

```
aatgtcggca gccaaggaga acccgtgcag gaaattccag gccaacatct tcaacaagag     60
caagtgtcag aactgcttca agccccgcga gtcgcatctg ctcaacgacg aggacctgac    120
gcaggcaaaa cccatttatg gcggttggct gctcctggct ccagatggga ccgactttga    180
caacccagtg caccggtctc ggaaatggca gcgacggttc ttcatccttt acgagcacgg    240
cctcttgcgc tacgccctgg atgagatgcc cacgaccctt cctcagggca ccatcaacat    300
gaaccagtgc acagatgtgg tggatgggga gggccgcacg ggccagaagt tctccctgtg    360
tattctgacg cctgagaagg agcatttcat ccgggcggag accaaggaga tcgtcagtgg    420
gtggctggag atgctcatgg tctatccccg gaccaacaag cagaatcaga agaagaaacg    480
gaaagtggag ccccccacac cacaggagcc tgggcctgcc aaggtggctg ttaccagcag    540
cagcagcagc agcagcagca gcagcagcat ccccagtgct gagaaagtcc ccaccaccaa    600
gtccacactc tggcaggaag aaatgaggac caaggaccag ccagatggca gcagcctgag    660
tccagctcag agtcccagcc agagccagcc tcctgctgcc agctccctgc gggaacctgg    720
gctagagagc aaagaagagg agagcgccat gagtagcgac cgcatggact gtggccgcaa    780
agtccgggtg gagagcggct acttctctct ggagaagacc aaacaggact tgaaggctga    840
agaacagcag ctgcccccgc cgctctcccc tcccagcccc agcaccccca accacaggag    900
gtcccaggtg attgaaaagt ttgaggcctt ggacattgag aaggcagagc acatggagac    960
caatgcagtg gggccctcac catccagcga cacacgccag ggccgcagcg agaagagggc   1020
gttccctagg aagcgggact tcaccaatga agccccccca gctcctctcc cagacgcctc   1080
ggcttccccc ctgtctccac accgaagagc caagtcactg gacaggaggt ccacggagcc   1140
ctccgtgacg cccgacctgc tgaatttcaa gaaaggctgg ctgactaagc agtatgagga   1200
cggccagtgg aagaaacact ggtttgtcct cgccgatcaa agcctgagat actacaggga   1260
ttcagtggct gaggaggcag ccgacttgga tggagaaatt gacttgtccg catgttacga   1320
tgtcacagag tatccagttc agagaaacta tggcttccag atacatacaa aggagggcga   1380
gtttaccctg tcggccatga catctgggat tcggcggaac tggatccaga ccatcatgaa   1440
gcacgtgcac ccgaccactg ccccggatgt gaccagctcg ttgccagagg aaaaaaacaa   1500
gagcagctgc tcttttgaga cctgcccgag gcctactgag aagcaagagg cagagctggg   1560
ggagccggac cctgagcaga agaggagccg cgcacgggag cggaggcgag agggccgctc   1620
caagaccttt gactgggctg agttccgtcc catccagcag gccctggctc aggagcgggt   1680
gggcggcgtg gggcctgctg acacccacga gcccctgcgc cctgaggcgg agcctgggga   1740
gctggagcgg gagcgtgcac ggaggcggga ggagcgccgc aagcgcttcg ggatgctcga   1800
cgccacagac gggccaggca ctgaggatgc agccctgcgc atggaggtgg accggagccc   1860
agggctgcct atgagcgacc tcaaaacgca taacgtccac gtggagattg agcagcggtg   1920
gcatcaggtg gagaccacac ctctccggga agagaagcag gtgcccatcg cccccgtcca   1980
cctgtcttct gaagatgggg gtgaccggct ctccacacac gagctgacct ctctgctcga   2040
gaaggagctg gagcagagcc agaaggaggc ctcagacctt ctggagcaga accggctcct   2100
gcaggaccag ctgagggtgg ccctgggccg ggagcagagc gcccgtgagg gctacgtgct   2160
gcaggccacg tgcgagcgag ggtttgcagc aatggaagaa acgcaccaga agaagattga   2220
```

-continued agatctccag aggcagcacc agcgggagct agagaaactt cgagaagaga aagaccgcct 2280
cctagccgag gagacagcgg ccaccatctc agccatcgaa gccatgaaga acgcccaccg 2340
ggaggaaatg gagcgggagc tggagaagag ccagcggtcc cagatcagca gcgtcaactc 2400
ggatgttgag gccctgcggc gccagtacct ggaggagctg cagtcggtgc agcgggaact 2460
ggaggtcctc tcggagcagt actcgcagaa gtgcctggag aatgcccatc tggcccaggc 2520
gctggaggcc gagcggcagg ccctgcggca gtgccagcgt gagaaccagg agctcaatgc 2580
ccacaaccag gagctgaaca accgcctggc tgcagagatc acacggttgc ggacgctgct 2640
gactggggac ggcggtgggg aggccactgg gtcacccctt gcacagggca aggatgccta 2700
tgaactagag gtcttattgc gggtaaagga atcggaaata cagtacctga aacaggagat 2760
tagctccctc aaggatgagc tgcagacggc actgcgggac aagaagtacg caagtgacaa 2820
gtacaaagac atctacacag agctcagcat cgcgaaggct aaggctgact gtgacatcag 2880
caggttgaag gagcagctca aggctgcaac ggaagcactg ggggagaagt cccctgacag 2940
tgccacggtg tccggatatg atataatgaa atctaaaagc aaccctgact tcttgaagaa 3000
agacagatcc tgtgtcaccc ggcaactcag aaacatcagg tccaaggatg caattcgaag 3060
tcacagcgaa tcagcctcac cttcagccct gtccagtagc cccaacaatc tgagcccaac 3120
aggctggtca cagccgaaaa cccccgtgcc agcacaaaga gagcgggcac cagtatctgg 3180
gacccaggag aaaaacaaaa ttaggcctcg tggacagaga gattcaagct attattggga 3240
aatagaagcc agtgaagtga tgctgtccac tcggattggg tcaggctctt ttggaactgt 3300
ttataagggt aaatggcacg gagatgttgc agtaaagatc ctaaaggttg tcgacccaac 3360
cccagagcaa ttccaggcct tcaggaatga ggtggctgtt ctgcgcaaaa cacggcatgt 3420
gaacattctg cttttcatgg ggtacatgac aaaggacaac ctggcaattg tgacccagtg 3480
gtgcgagggc agcagcctct acaaacacct gcatgtccag gagaccaagt ttcagatgtt 3540
ccagctaatt gacattgccc ggcagacggc tcagggaatg gactatttgc atgcaaagaa 3600
catcatccat agagacatga aatccaacaa tatatttctc catgaaggct taacagtgaa 3660
aattggagat tttggtttgg caacagtaaa gtcacgctgg agtggttctc agcaggttga 3720
acaacctact ggctctgtcc tctggatggc cccagaggtg atccgaatgc aggataacaa 3780
cccattcagt ttccagtcgg atgtctactc ctatggcatc gtattgtatg aactgatgac 3840
gggggagctt ccttattctc acatcaacaa ccgagatcag atcatcttca tggtgggccg 3900
aggatatgcc tccccagatc ttagtaagct atataagaac tgccccaaag caatgaagag 3960
gctggtagct gactgtgtga agaaagtaaa ggaagagagg cctctttttc cccagatcct 4020
gtcttccatt gagctgctcc aacactctct accgaagatc aaccggagcg cttccgagcc 4080
atccttgcat cgggcagccc acactgagga tatcaatgct tgcacgctga ccacgtcccc 4140
gaggctgcct gtcttctag 4159

<210> SEQ ID NO 6
<211> LENGTH: 1385
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 6

Met Ser Ala Ala Lys Glu Asn Pro Cys Arg Lys Phe Gln Ala Asn Ile

-continued

```
1               5                   10                  15

Phe Asn Lys Ser Lys Cys Gln Asn Cys Phe Lys Pro Arg Glu Ser His
            20                  25                  30

Leu Leu Asn Asp Glu Asp Leu Thr Gln Ala Lys Pro Ile Tyr Gly Gly
        35                  40                  45

Trp Leu Leu Leu Ala Pro Asp Gly Thr Asp Phe Asp Asn Pro Val His
    50                  55                  60

Arg Ser Arg Lys Trp Gln Arg Arg Phe Phe Ile Leu Tyr Glu His Gly
65                  70                  75                  80

Leu Leu Arg Tyr Ala Leu Asp Glu Met Pro Thr Thr Leu Pro Gln Gly
                85                  90                  95

Thr Ile Asn Met Asn Gln Cys Thr Asp Val Val Asp Gly Glu Gly Arg
            100                 105                 110

Thr Gly Gln Lys Phe Ser Leu Cys Ile Leu Thr Pro Glu Lys Glu His
        115                 120                 125

Phe Ile Arg Ala Glu Thr Lys Glu Ile Val Ser Gly Trp Leu Glu Met
    130                 135                 140

Leu Met Val Tyr Pro Arg Thr Asn Lys Gln Asn Gln Lys Lys Lys Arg
145                 150                 155                 160

Lys Val Glu Pro Pro Thr Pro Gln Glu Pro Gly Pro Ala Lys Val Ala
                165                 170                 175

Val Thr Ser Ser Ser Ser Ser Ser Ser Ser Ser Ser Ser Ile Pro Ser
            180                 185                 190

Ala Glu Lys Val Pro Thr Thr Lys Ser Thr Leu Trp Gln Glu Glu Met
        195                 200                 205

Arg Thr Lys Asp Gln Pro Asp Gly Ser Ser Leu Ser Pro Ala Gln Ser
    210                 215                 220

Pro Ser Gln Ser Gln Pro Pro Ala Ala Ser Ser Leu Arg Glu Pro Gly
225                 230                 235                 240

Leu Glu Ser Lys Glu Glu Glu Ser Ala Met Ser Ser Asp Arg Met Asp
                245                 250                 255

Cys Gly Arg Lys Val Arg Val Glu Ser Gly Tyr Phe Ser Leu Glu Lys
            260                 265                 270

Thr Lys Gln Asp Leu Lys Ala Glu Glu Gln Gln Leu Pro Pro Pro Leu
        275                 280                 285

Ser Pro Pro Ser Pro Ser Thr Pro Asn His Arg Arg Ser Gln Val Ile
    290                 295                 300

Glu Lys Phe Glu Ala Leu Asp Ile Glu Lys Ala Glu His Met Glu Thr
305                 310                 315                 320

Asn Ala Val Gly Pro Ser Pro Ser Ser Asp Thr Arg Gln Gly Arg Ser
                325                 330                 335

Glu Lys Arg Ala Phe Pro Arg Lys Arg Asp Phe Thr Asn Glu Ala Pro
            340                 345                 350

Pro Ala Pro Leu Pro Asp Ala Ser Ala Ser Pro Leu Ser Pro His Arg
        355                 360                 365

Arg Ala Lys Ser Leu Asp Arg Arg Ser Thr Glu Pro Ser Val Thr Pro
    370                 375                 380

Asp Leu Leu Asn Phe Lys Lys Gly Trp Leu Thr Lys Gln Tyr Glu Asp
385                 390                 395                 400

Gly Gln Trp Lys Lys His Trp Phe Val Leu Ala Asp Gln Ser Leu Arg
                405                 410                 415

Tyr Tyr Arg Asp Ser Val Ala Glu Glu Ala Ala Asp Leu Asp Gly Glu
            420                 425                 430
```

```
Ile Asp Leu Ser Ala Cys Tyr Asp Val Thr Glu Tyr Pro Val Gln Arg
        435                 440                 445

Asn Tyr Gly Phe Gln Ile His Thr Lys Glu Gly Glu Phe Thr Leu Ser
    450                 455                 460

Ala Met Thr Ser Gly Ile Arg Arg Asn Trp Ile Gln Thr Ile Met Lys
465                 470                 475                 480

His Val His Pro Thr Thr Ala Pro Asp Val Thr Ser Ser Leu Pro Glu
                485                 490                 495

Glu Lys Asn Lys Ser Ser Cys Ser Phe Glu Thr Cys Pro Arg Pro Thr
            500                 505                 510

Glu Lys Gln Glu Ala Glu Leu Gly Glu Pro Asp Pro Glu Gln Lys Arg
        515                 520                 525

Ser Arg Ala Arg Glu Arg Arg Arg Glu Gly Arg Ser Lys Thr Phe Asp
    530                 535                 540

Trp Ala Glu Phe Arg Pro Ile Gln Gln Ala Leu Ala Gln Glu Arg Val
545                 550                 555                 560

Gly Gly Val Gly Pro Ala Asp Thr His Glu Pro Leu Arg Pro Glu Ala
                565                 570                 575

Glu Pro Gly Glu Leu Glu Arg Glu Arg Ala Arg Arg Arg Glu Glu Arg
            580                 585                 590

Arg Lys Arg Phe Gly Met Leu Asp Ala Thr Asp Gly Pro Gly Thr Glu
        595                 600                 605

Asp Ala Ala Leu Arg Met Glu Val Asp Arg Ser Pro Gly Leu Pro Met
    610                 615                 620

Ser Asp Leu Lys Thr His Asn Val His Val Glu Ile Glu Gln Arg Trp
625                 630                 635                 640

His Gln Val Glu Thr Thr Pro Leu Arg Glu Glu Lys Gln Val Pro Ile
                645                 650                 655

Ala Pro Val His Leu Ser Ser Glu Asp Gly Gly Asp Arg Leu Ser Thr
            660                 665                 670

His Glu Leu Thr Ser Leu Leu Glu Lys Glu Leu Glu Gln Ser Gln Lys
        675                 680                 685

Glu Ala Ser Asp Leu Leu Glu Gln Asn Arg Leu Leu Gln Asp Gln Leu
    690                 695                 700

Arg Val Ala Leu Gly Arg Glu Gln Ser Ala Arg Glu Gly Tyr Val Leu
705                 710                 715                 720

Gln Ala Thr Cys Glu Arg Gly Phe Ala Ala Met Glu Glu Thr His Gln
                725                 730                 735

Lys Lys Ile Glu Asp Leu Gln Arg Gln His Gln Arg Glu Leu Glu Lys
            740                 745                 750

Leu Arg Glu Glu Lys Asp Arg Leu Leu Ala Glu Glu Thr Ala Ala Thr
        755                 760                 765

Ile Ser Ala Ile Glu Ala Met Lys Asn Ala His Arg Glu Glu Met Glu
    770                 775                 780

Arg Glu Leu Glu Lys Ser Gln Arg Ser Gln Ile Ser Ser Val Asn Ser
785                 790                 795                 800

Asp Val Glu Ala Leu Arg Arg Gln Tyr Leu Glu Glu Leu Gln Ser Val
                805                 810                 815

Gln Arg Glu Leu Glu Val Leu Ser Glu Gln Tyr Ser Gln Lys Cys Leu
            820                 825                 830

Glu Asn Ala His Leu Ala Gln Ala Leu Glu Ala Glu Arg Gln Ala Leu
        835                 840                 845
```

-continued

```
Arg Gln Cys Gln Arg Glu Asn Gln Glu Leu Asn Ala His Asn Gln Glu
    850                 855                 860

Leu Asn Asn Arg Leu Ala Ala Glu Ile Thr Arg Leu Arg Thr Leu Leu
865                 870                 875                 880

Thr Gly Asp Gly Gly Gly Glu Ala Thr Gly Ser Pro Leu Ala Gln Gly
                885                 890                 895

Lys Asp Ala Tyr Glu Leu Glu Val Leu Leu Arg Val Lys Glu Ser Glu
            900                 905                 910

Ile Gln Tyr Leu Lys Gln Glu Ile Ser Ser Leu Lys Asp Glu Leu Gln
        915                 920                 925

Thr Ala Leu Arg Asp Lys Lys Tyr Ala Ser Asp Lys Tyr Lys Asp Ile
    930                 935                 940

Tyr Thr Glu Leu Ser Ile Ala Lys Ala Lys Ala Asp Cys Asp Ile Ser
945                 950                 955                 960

Arg Leu Lys Glu Gln Leu Lys Ala Ala Thr Glu Ala Leu Gly Glu Lys
                965                 970                 975

Ser Pro Asp Ser Ala Thr Val Ser Gly Tyr Asp Ile Met Lys Ser Lys
            980                 985                 990

Ser Asn Pro Asp Phe Leu Lys Lys  Asp Arg Ser Cys Val  Thr Arg Gln
        995                 1000                1005

Leu Arg  Asn Ile Arg Ser Lys  Asp Ala Ile Arg Ser  His Ser Glu
    1010                1015                1020

Ser Ala  Ser Pro Ser Ala Leu  Ser Ser Ser Pro Asn  Asn Leu Ser
    1025                1030                1035

Pro Thr  Gly Trp Ser Gln Pro  Lys Thr Pro Val Pro  Ala Gln Arg
    1040                1045                1050

Glu Arg  Ala Pro Val Ser Gly  Thr Gln Glu Lys Asn  Lys Ile Arg
    1055                1060                1065

Pro Arg  Gly Gln Arg Asp Ser  Ser Tyr Tyr Trp Glu  Ile Glu Ala
    1070                1075                1080

Ser Glu  Val Met Leu Ser Thr  Arg Ile Gly Ser Gly  Ser Phe Gly
    1085                1090                1095

Thr Val  Tyr Lys Gly Lys Trp  His Gly Asp Val Ala  Val Lys Ile
    1100                1105                1110

Leu Lys  Val Val Asp Pro Thr  Pro Glu Gln Phe Gln  Ala Phe Arg
    1115                1120                1125

Asn Glu  Val Ala Val Leu Arg  Lys Thr Arg His Val  Asn Ile Leu
    1130                1135                1140

Leu Phe  Met Gly Tyr Met Thr  Lys Asp Asn Leu Ala  Ile Val Thr
    1145                1150                1155

Gln Trp  Cys Glu Gly Ser Ser  Leu Tyr Lys His Leu  His Val Gln
    1160                1165                1170

Glu Thr  Lys Phe Gln Met Phe  Gln Leu Ile Asp Ile  Ala Arg Gln
    1175                1180                1185

Thr Ala  Gln Gly Met Asp Tyr  Leu His Ala Lys Asn  Ile Ile His
    1190                1195                1200

Arg Asp  Met Lys Ser Asn Asn  Ile Phe Leu His Glu  Gly Leu Thr
    1205                1210                1215

Val Lys  Ile Gly Asp Phe Gly  Leu Ala Thr Val Lys  Ser Arg Trp
    1220                1225                1230

Ser Gly  Ser Gln Gln Val Glu  Gln Pro Thr Gly Ser  Val Leu Trp
    1235                1240                1245

Met Ala  Pro Glu Val Ile Arg  Met Gln Asp Asn Asn  Pro Phe Ser
```

1250 1255 1260

Phe Gln Ser Asp Val Tyr Ser Tyr Gly Ile Val Leu Tyr Glu Leu
1265 1270 1275

Met Thr Gly Glu Leu Pro Tyr Ser His Ile Asn Asn Arg Asp Gln
1280 1285 1290

Ile Ile Phe Met Val Gly Arg Gly Tyr Ala Ser Pro Asp Leu Ser
1295 1300 1305

Lys Leu Tyr Lys Asn Cys Pro Lys Ala Met Lys Arg Leu Val Ala
1310 1315 1320

Asp Cys Val Lys Lys Val Lys Glu Glu Arg Pro Leu Phe Pro Gln
1325 1330 1335

Ile Leu Ser Ser Ile Glu Leu Leu Gln His Ser Leu Pro Lys Ile
1340 1345 1350

Asn Arg Ser Ala Ser Glu Pro Ser Leu His Arg Ala Ala His Thr
1355 1360 1365

Glu Asp Ile Asn Ala Cys Thr Leu Thr Thr Ser Pro Arg Leu Pro
1370 1375 1380

Val Phe
1385

<210> SEQ ID NO 7
<211> LENGTH: 2226
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7
atgtcccctt gtcctgaaga agcagctatg agaagagagg tggtgaaacg gatcgaaact 60
gtggtgaaag acctttggcc gacggctgat gtacagatat ttggcagctt tagtacaggt 120
ctttatcttc caactagcga catagacctg gtggtcttcg ggaaatggga gcgtcctcct 180
ttacagctgc tggagcaagc cctgcggaag cacaacgtgg ctgagccgtg ttccatcaaa 240
gtccttgaca aggctacggt accaataata aagctcacag atcaggagac tgaagtgaaa 300
gttgacatca gctttaacat ggagacgggc gtccgggcag cggagttcat caagaattac 360
atgaagaaat attcattgct gccttacttg attttagtat tgaaacagtt ccttctgcag 420
agggacctga atgaagtttt tacaggtgga attagctcat acagcctaat tttaatggcc 480
attagctttc tacagttgca tccaagaatt gatgcccgga gagctgatga aaaccttgga 540
atgcttcttg tagaattttt tgaactctat gggagaaatt ttaattactt gaaaaccggt 600
attagaatca aagaaggagg tgcctatatc gccaaagagg agatcatgaa agccatgacc 660
agcgggtaca gaccgtcgat gctgtgcatt gaggaccccc tgctgccagg gaatgacgtt 720
ggccggagct cctatggcgc catgcaggtg aagcaggtct tcgattatgc ctacatagtg 780
ctcagccatg ctgtgtcacc gctggccagg tcctatccaa acagagacgc cgaaagtact 840
ttaggaagaa tcatcaaagt aactcaggag gtgattgact accggaggtg gatcaaagag 900
aagtggggca gcaaagccca cccgtcgcca ggcatggaca gcaggatcaa gatcaaagag 960
cgaatagcca catgcaatgg ggagcagacg cagaaccgag agcccgagtc tccctatggc 1020
cagcgcttga ctttgtcgct gtccagcccc cagctcctgt cttcaggctc ctcggcctct 1080
tctgtgtctt cactttctgg gagtgacgtt gattcagaca caccgccctg cacaacgccc 1140
agtgtttacc agttcagtct gcaagcgcca gctcctctca tggccggctt acccaccgcc 1200
ttgccaatgc ccagtggcaa acctcagccc accacttcca gaacactgat catgacaacc 1260
aacaatcaga ggcctcgtgg acagagagat tcaagctatt attgggaaat agaagccagt 1320
gaagtgatgc tgtccactcg gattgggtca ggctcttttg gaactgttta taagggtaaa 1380
tggcacggag atgttgcagt aaagatccta aaggttgtcg acccaacccc agagcaattc 1440
caggccttca ggaatgaggt ggctgttctg cgcaaaacac ggcatgtgaa cattctgctt 1500
ttcatggggt acatgacaaa ggacaacctg gcaattgtga cccagtggtg cgagggcagc 1560
agcctctaca aacacctgca tgtccaggag accaagtttc agatgttcca gctaattgac 1620
attgcccggc agacggctca gggaatggac tatttgcatg caaagaacat catccataga 1680
gacatgaaat ccaacaatat atttctccat gaaggcttaa cagtgaaaat tggagatttt 1740
ggtttggcaa cagtaaagtc acgctggagt ggttctcagc aggttgaaca acctactggc 1800
tctgtcctct ggatggcccc agaggtgatc cgaatgcagg ataacaaccc attcagtttc 1860
cagtcggatg tctactccta tggcatcgta ttgtatgaac tgatgacggg ggagcttcct 1920
tattctcaca tcaacaaccg agatcagatc atcttcatgg tgggccgagg atatgcctcc 1980
ccagatctta gtaagctata taagaactgc cccaaagcaa tgaagaggct ggtagctgac 2040
tgtgtgaaga aagtaaagga agagaggcct ctttttcccc agatcctgtc ttccattgag 2100
ctgctccaac actctctacc gaagatcaac cggagcgctt ccgagccatc cttgcatcgg 2160
gcagcccaca ctgaggatat caatgcttgc acgctgacca cgtccccgag gctgcctgtc 2220
ttctag 2226

<210> SEQ ID NO 8
<211> LENGTH: 741
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

Met Ser Pro Cys Pro Glu Glu Ala Ala Met Arg Arg Glu Val Val Lys
1 5 10 15

Arg Ile Glu Thr Val Val Lys Asp Leu Trp Pro Thr Ala Asp Val Gln
20 25 30

Ile Phe Gly Ser Phe Ser Thr Gly Leu Tyr Leu Pro Thr Ser Asp Ile
35 40 45

Asp Leu Val Val Phe Gly Lys Trp Glu Arg Pro Pro Leu Gln Leu Leu
50 55 60

Glu Gln Ala Leu Arg Lys His Asn Val Ala Glu Pro Cys Ser Ile Lys
65 70 75 80

Val Leu Asp Lys Ala Thr Val Pro Ile Ile Lys Leu Thr Asp Gln Glu
85 90 95

Thr Glu Val Lys Val Asp Ile Ser Phe Asn Met Glu Thr Gly Val Arg
100 105 110

Ala Ala Glu Phe Ile Lys Asn Tyr Met Lys Lys Tyr Ser Leu Leu Pro
115 120 125

Tyr Leu Ile Leu Val Leu Lys Gln Phe Leu Leu Gln Arg Asp Leu Asn
130 135 140

Glu Val Phe Thr Gly Gly Ile Ser Ser Tyr Ser Leu Ile Leu Met Ala
145 150 155 160

-continued

```
Ile Ser Phe Leu Gln Leu His Pro Arg Ile Asp Ala Arg Arg Ala Asp
                165                 170                 175

Glu Asn Leu Gly Met Leu Leu Val Glu Phe Phe Glu Leu Tyr Gly Arg
            180                 185                 190

Asn Phe Asn Tyr Leu Lys Thr Gly Ile Arg Ile Lys Glu Gly Gly Ala
        195                 200                 205

Tyr Ile Ala Lys Glu Glu Ile Met Lys Ala Met Thr Ser Gly Tyr Arg
    210                 215                 220

Pro Ser Met Leu Cys Ile Glu Asp Pro Leu Leu Pro Gly Asn Asp Val
225                 230                 235                 240

Gly Arg Ser Ser Tyr Gly Ala Met Gln Val Lys Gln Val Phe Asp Tyr
                245                 250                 255

Ala Tyr Ile Val Leu Ser His Ala Val Ser Pro Leu Ala Arg Ser Tyr
            260                 265                 270

Pro Asn Arg Asp Ala Glu Ser Thr Leu Gly Arg Ile Ile Lys Val Thr
        275                 280                 285

Gln Glu Val Ile Asp Tyr Arg Arg Trp Ile Lys Glu Lys Trp Gly Ser
    290                 295                 300

Lys Ala His Pro Ser Pro Gly Met Asp Ser Arg Ile Lys Ile Lys Glu
305                 310                 315                 320

Arg Ile Ala Thr Cys Asn Gly Glu Gln Thr Gln Asn Arg Glu Pro Glu
                325                 330                 335

Ser Pro Tyr Gly Gln Arg Leu Thr Leu Ser Leu Ser Ser Pro Gln Leu
            340                 345                 350

Leu Ser Ser Gly Ser Ser Ala Ser Ser Val Ser Ser Leu Ser Gly Ser
        355                 360                 365

Asp Val Asp Ser Asp Thr Pro Pro Cys Thr Thr Pro Ser Val Tyr Gln
    370                 375                 380

Phe Ser Leu Gln Ala Pro Ala Pro Leu Met Ala Gly Leu Pro Thr Ala
385                 390                 395                 400

Leu Pro Met Pro Ser Gly Lys Pro Gln Pro Thr Thr Ser Arg Thr Leu
                405                 410                 415

Ile Met Thr Thr Asn Asn Gln Arg Pro Arg Gly Gln Arg Asp Ser Ser
            420                 425                 430

Tyr Tyr Trp Glu Ile Glu Ala Ser Glu Val Met Leu Ser Thr Arg Ile
        435                 440                 445

Gly Ser Gly Ser Phe Gly Thr Val Tyr Lys Gly Lys Trp His Gly Asp
    450                 455                 460

Val Ala Val Lys Ile Leu Lys Val Val Asp Pro Thr Pro Glu Gln Phe
465                 470                 475                 480

Gln Ala Phe Arg Asn Glu Val Ala Val Leu Arg Lys Thr Arg His Val
                485                 490                 495

Asn Ile Leu Leu Phe Met Gly Tyr Met Thr Lys Asp Asn Leu Ala Ile
            500                 505                 510

Val Thr Gln Trp Cys Glu Gly Ser Ser Leu Tyr Lys His Leu His Val
        515                 520                 525

Gln Glu Thr Lys Phe Gln Met Phe Gln Leu Ile Asp Ile Ala Arg Gln
    530                 535                 540

Thr Ala Gln Gly Met Asp Tyr Leu His Ala Lys Asn Ile Ile His Arg
545                 550                 555                 560

Asp Met Lys Ser Asn Asn Ile Phe Leu His Glu Gly Leu Thr Val Lys
                565                 570                 575
```

-continued

```
Ile Gly Asp Phe Gly Leu Ala Thr Val Lys Ser Arg Trp Ser Gly Ser
            580                 585                 590

Gln Gln Val Glu Gln Pro Thr Gly Ser Val Leu Trp Met Ala Pro Glu
        595                 600                 605

Val Ile Arg Met Gln Asp Asn Asn Pro Phe Ser Phe Gln Ser Asp Val
    610                 615                 620

Tyr Ser Tyr Gly Ile Val Leu Tyr Glu Leu Met Thr Gly Glu Leu Pro
625                 630                 635                 640

Tyr Ser His Ile Asn Asn Arg Asp Gln Ile Ile Phe Met Val Gly Arg
                645                 650                 655

Gly Tyr Ala Ser Pro Asp Leu Ser Lys Leu Tyr Lys Asn Cys Pro Lys
            660                 665                 670

Ala Met Lys Arg Leu Val Ala Asp Cys Val Lys Lys Val Lys Glu Glu
        675                 680                 685

Arg Pro Leu Phe Pro Gln Ile Leu Ser Ser Ile Glu Leu Leu Gln His
    690                 695                 700

Ser Leu Pro Lys Ile Asn Arg Ser Ala Ser Glu Pro Ser Leu His Arg
705                 710                 715                 720

Ala Ala His Thr Glu Asp Ile Asn Ala Cys Thr Leu Thr Thr Ser Pro
                725                 730                 735

Arg Leu Pro Val Phe
            740
```

<210> SEQ ID NO 9
<211> LENGTH: 1260
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
atggcggggt gcagggggtc tctgtgctgc tgctgcaggt ggtgctgctg ctgcggtgag     60

cgtgagaccc gcacccccga ggagctgacc atccttggag aaacacagga ggaggaggat    120

gagattcttc caaggaaaga ctatgaggat gcaattcgaa gtcacagcga atcagcctca    180

ccttcagccc tgtccagtag ccccaacaat ctgagcccaa caggctggtc acagccgaaa    240

acccccgtgc cagcacaaag agagcgggca ccagtatctg ggacccagga gaaaaacaaa    300

attaggcctc gtggacagag agattcaagc tattattggg aaatagaagc cagtgaagtg    360

atgctgtcca ctcggattgg gtcaggctct tttggaactg tttataaggg taaatggcac    420

ggagatgttg cagtaaagat cctaaaggtt gtcgacccaa ccccagagca attccaggcc    480

ttcaggaatg aggtggctgt tctgcgcaaa acacggcatg tgaacattct gcttttcatg    540

gggtacatga caaaggacaa cctggcaatt gtgacccagt ggtgcgaggg cagcagcctc    600

tacaaacacc tgcatgtcca ggagaccaag tttcagatgt tccagctaat tgacattgcc    660

cggcagacgg ctcagggaat ggactatttg catgcaaaga acatcatcca tagagacatg    720

aaatccaaca atatatttct ccatgaaggc ttaacagtga aaattggaga ttttggtttg    780

gcaacagtaa agtcacgctg gagtggttct cagcaggttg aacaacctac tggctctgtc    840

ctctggatgg ccccagaggt gatccgaatg caggataaca acccattcag tttccagtcg    900

gatgtctact cctatggcat cgtattgtat gaactgatga cgggggagct tccttattct    960

cacatcaaca accgagatca gatcatcttc atggtgggcc gaggatatgc ctccccagat   1020
```

-continued cttagtaagc tatataagaa ctgccccaaa gcaatgaaga ggctggtagc tgactgtgtg 1080
aagaaagtaa aggaagagag gcctcttttt ccccagatcc tgtcttccat tgagctgctc 1140
caacactctc taccgaagat caaccggagc gcttccgagc catccttgca tcgggcagcc 1200
cacactgagg atatcaatgc ttgcacgctg accacgtccc cgaggctgcc tgtcttctag 1260

<210> SEQ ID NO 10
<211> LENGTH: 419
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 10

Met Ala Gly Cys Arg Gly Ser Leu Cys Cys Cys Cys Arg Trp Cys Cys
1 5 10 15

Cys Cys Gly Glu Arg Glu Thr Arg Thr Pro Glu Glu Leu Thr Ile Leu
20 25 30

Gly Glu Thr Gln Glu Glu Glu Asp Glu Ile Leu Pro Arg Lys Asp Tyr
35 40 45

Glu Asp Ala Ile Arg Ser His Ser Glu Ser Ala Ser Pro Ser Ala Leu
50 55 60

Ser Ser Ser Pro Asn Asn Leu Ser Pro Thr Gly Trp Ser Gln Pro Lys
65 70 75 80

Thr Pro Val Pro Ala Gln Arg Glu Arg Ala Pro Val Ser Gly Thr Gln
85 90 95

Glu Lys Asn Lys Ile Arg Pro Arg Gly Gln Arg Asp Ser Ser Tyr Tyr
100 105 110

Trp Glu Ile Glu Ala Ser Glu Val Met Leu Ser Thr Arg Ile Gly Ser
115 120 125

Gly Ser Phe Gly Thr Val Tyr Lys Gly Lys Trp His Gly Asp Val Ala
130 135 140

Val Lys Ile Leu Lys Val Val Asp Pro Thr Pro Glu Gln Phe Gln Ala
145 150 155 160

Phe Arg Asn Glu Val Ala Val Leu Arg Lys Thr Arg His Val Asn Ile
165 170 175

Leu Leu Phe Met Gly Tyr Met Thr Lys Asp Asn Leu Ala Ile Val Thr
180 185 190

Gln Trp Cys Glu Gly Ser Ser Leu Tyr Lys His Leu His Val Gln Glu
195 200 205

Thr Lys Phe Gln Met Phe Gln Leu Ile Asp Ile Ala Arg Gln Thr Ala
210 215 220

Gln Gly Met Asp Tyr Leu His Ala Lys Asn Ile Ile His Arg Asp Met
225 230 235 240

Lys Ser Asn Asn Ile Phe Leu His Glu Gly Leu Thr Val Lys Ile Gly
245 250 255

Asp Phe Gly Leu Ala Thr Val Lys Ser Arg Trp Ser Gly Ser Gln Gln
260 265 270

Val Glu Gln Pro Thr Gly Ser Val Leu Trp Met Ala Pro Glu Val Ile
275 280 285

Arg Met Gln Asp Asn Asn Pro Phe Ser Phe Gln Ser Asp Val Tyr Ser
290 295 300

Tyr Gly Ile Val Leu Tyr Glu Leu Met Thr Gly Glu Leu Pro Tyr Ser
305 310 315 320

His Ile Asn Asn Arg Asp Gln Ile Ile Phe Met Val Gly Arg Gly Tyr
325 330 335

Ala Ser Pro Asp Leu Ser Lys Leu Tyr Lys Asn Cys Pro Lys Ala Met
340 345 350

Lys Arg Leu Val Ala Asp Cys Val Lys Lys Val Lys Glu Glu Arg Pro
355 360 365

Leu Phe Pro Gln Ile Leu Ser Ser Ile Glu Leu Leu Gln His Ser Leu
370 375 380

Pro Lys Ile Asn Arg Ser Ala Ser Glu Pro Ser Leu His Arg Ala Ala
385 390 395 400

His Thr Glu Asp Ile Asn Ala Cys Thr Leu Thr Thr Ser Pro Arg Leu
405 410 415

Pro Val Phe

<210> SEQ ID NO 11
<211> LENGTH: 2088
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
atggcattgg tttttcaatt cgggcagccc gtcagggctc agcctctgcc aggactctgc 60
cacggcaagc tcattcggac aaacgcctgt gatgtgtgca acagcaccga tcttccggaa 120
gtcgagatca ttagcctgct ggaggagcag ctgccccatt ataagttaag agccgacacc 180
atctacggtt atgaccacga cgactggctc catacacctc tcatttctcc agatgccaac 240
attgacctca caaccgagca aattgaagag acgttaaaat acttcctttt atgtgctgaa 300
agagttggcc agatgactaa gacatataat gacatagatg ctgtcactcg gcttcttgag 360
gagaaagagc gggatttaga attggccgct cgcatcggcc agtcgttgtt gaagaagaac 420
aagaccctaa ccgagaggaa cgagctgctg gaggagcagg tggaacacat cagggaggag 480
gtgtctcagc tccggcatga gctgtccatg aaggatgagc tgcttcagtt ctacaccagc 540
gctgcggagg agagtgagcc cgagtccgtt tgctcaaccc cgttgaagag gaatgagtcg 600
tcctcctcag tccagaatta ctttcatttg gattctcttc aaaagaagct gaaagacctt 660
gaagaggaga atgttgtact tcgatccgag gccagccagc tgaagacaga gaccatcacc 720
tatgaggaga aggagcagca gctggtcaat gactgcgtga aggagctgag ggatgccaat 780
gtccagattg ctagtatctc agaggaactg gccaagaaga cggaagatgc tgcccgccag 840
caagaggaga tcacacacct gctatcgcaa atagttgatt tgcagaaaaa ggcaaaagct 900
tgcgcagtgg aaaatgaaga acttgtccag catctggggg ctgctaagga tgcccagcgg 960
cagctcacag ccgaggatgc aattcgaagt cacagcgaat cagcctcacc ttcagccctg 1020
tccagtagcc ccaacaatct gagcccaaca ggctggtcac agccgaaaac ccccgtgcca 1080
gcacaaagag agcgggcacc agtatctggg acccaggaga aaaacaaaat taggcctcgt 1140
ggacagagag attcaagcta ttattgggaa atagaagcca gtgaagtgat gctgtccact 1200
cggattgggt caggctcttt tggaactgtt tataagggta aatggcacgg agatgttgca 1260
gtaaagatcc taaaggttgt cgacccaacc ccagagcaat tccaggcctt caggaatgag 1320
gtggctgttc tgcgcaaaac acggcatgtg aacattctgc ttttcatggg gtacatgaca 1380

```
aaggacaacc tggcaattgt gacccagtgg tgcgagggca gcagcctcta caaacacctg   1440

catgtccagg agaccaagtt tcagatgttc cagctaattg acattgcccg gcagacggct   1500

cagggaatgg actatttgca tgcaaagaac atcatccata gagacatgaa atccaacaat   1560

atatttctcc atgaaggctt aacagtgaaa attggagatt ttggtttggc aacagtaaag   1620

tcacgctgga gtggttctca gcaggttgaa caacctactg gctctgtcct ctggatggcc   1680

ccagaggtga tccgaatgca ggataacaac ccattcagtt tccagtcgga tgtctactcc   1740

tatggcatcg tattgtatga actgatgacg gggagcttc cttattctca catcaacaac   1800

cgagatcaga tcatcttcat ggtgggccga ggatatgcct ccccagatct tagtaagcta   1860

tataagaact gccccaaagc aatgaagagg ctggtagctg actgtgtgaa gaaagtaaag   1920

gaagagaggc ctctttttcc ccagatcctg tcttccattg agctgctcca acactctcta   1980

ccgaagatca accggagcgc ttccgagcca tccttgcatc gggcagccca cactgaggat   2040

atcaatgctt gcacgctgac cacgtccccg aggctgcctg tcttctag               2088
```

```
<210> SEQ ID NO 12
<211> LENGTH: 695
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Ala Leu Val Phe Gln Phe Gly Gln Pro Val Arg Ala Gln Pro Leu
1               5                   10                  15

Pro Gly Leu Cys His Gly Lys Leu Ile Arg Thr Asn Ala Cys Asp Val
            20                  25                  30

Cys Asn Ser Thr Asp Leu Pro Glu Val Glu Ile Ile Ser Leu Leu Glu
        35                  40                  45

Glu Gln Leu Pro His Tyr Lys Leu Arg Ala Asp Thr Ile Tyr Gly Tyr
    50                  55                  60

Asp His Asp Asp Trp Leu His Thr Pro Leu Ile Ser Pro Asp Ala Asn
65                  70                  75                  80

Ile Asp Leu Thr Thr Glu Gln Ile Glu Glu Thr Leu Lys Tyr Phe Leu
                85                  90                  95

Leu Cys Ala Glu Arg Val Gly Gln Met Thr Lys Thr Tyr Asn Asp Ile
            100                 105                 110

Asp Ala Val Thr Arg Leu Leu Glu Glu Lys Glu Arg Asp Leu Glu Leu
        115                 120                 125

Ala Ala Arg Ile Gly Gln Ser Leu Leu Lys Lys Asn Lys Thr Leu Thr
    130                 135                 140

Glu Arg Asn Glu Leu Leu Glu Glu Gln Val Glu His Ile Arg Glu Glu
145                 150                 155                 160

Val Ser Gln Leu Arg His Glu Leu Ser Met Lys Asp Glu Leu Leu Gln
                165                 170                 175

Phe Tyr Thr Ser Ala Ala Glu Glu Ser Glu Pro Glu Ser Val Cys Ser
            180                 185                 190

Thr Pro Leu Lys Arg Asn Glu Ser Ser Ser Ser Val Gln Asn Tyr Phe
        195                 200                 205

His Leu Asp Ser Leu Gln Lys Lys Leu Lys Asp Leu Glu Glu Glu Asn
    210                 215                 220

Val Val Leu Arg Ser Glu Ala Ser Gln Leu Lys Thr Glu Thr Ile Thr
```

-continued

```
225                 230                 235                 240

Tyr Glu Glu Lys Glu Gln Gln Leu Val Asn Asp Cys Val Lys Glu Leu
                245                 250                 255

Arg Asp Ala Asn Val Gln Ile Ala Ser Ile Ser Glu Glu Leu Ala Lys
            260                 265                 270

Lys Thr Glu Asp Ala Ala Arg Gln Gln Glu Glu Ile Thr His Leu Leu
        275                 280                 285

Ser Gln Ile Val Asp Leu Gln Lys Lys Ala Lys Ala Cys Ala Val Glu
    290                 295                 300

Asn Glu Glu Leu Val Gln His Leu Gly Ala Ala Lys Asp Ala Gln Arg
305                 310                 315                 320

Gln Leu Thr Ala Glu Asp Ala Ile Arg Ser His Ser Glu Ser Ala Ser
                325                 330                 335

Pro Ser Ala Leu Ser Ser Ser Pro Asn Asn Leu Ser Pro Thr Gly Trp
            340                 345                 350

Ser Gln Pro Lys Thr Pro Val Pro Ala Gln Arg Glu Arg Ala Pro Val
        355                 360                 365

Ser Gly Thr Gln Glu Lys Asn Lys Ile Arg Pro Arg Gly Gln Arg Asp
    370                 375                 380

Ser Ser Tyr Tyr Trp Glu Ile Glu Ala Ser Glu Val Met Leu Ser Thr
385                 390                 395                 400

Arg Ile Gly Ser Gly Ser Phe Gly Thr Val Tyr Lys Gly Lys Trp His
                405                 410                 415

Gly Asp Val Ala Val Lys Ile Leu Lys Val Val Asp Pro Thr Pro Glu
            420                 425                 430

Gln Phe Gln Ala Phe Arg Asn Glu Val Ala Val Leu Arg Lys Thr Arg
        435                 440                 445

His Val Asn Ile Leu Leu Phe Met Gly Tyr Met Thr Lys Asp Asn Leu
    450                 455                 460

Ala Ile Val Thr Gln Trp Cys Glu Gly Ser Ser Leu Tyr Lys His Leu
465                 470                 475                 480

His Val Gln Glu Thr Lys Phe Gln Met Phe Gln Leu Ile Asp Ile Ala
                485                 490                 495

Arg Gln Thr Ala Gln Gly Met Asp Tyr Leu His Ala Lys Asn Ile Ile
            500                 505                 510

His Arg Asp Met Lys Ser Asn Asn Ile Phe Leu His Glu Gly Leu Thr
        515                 520                 525

Val Lys Ile Gly Asp Phe Gly Leu Ala Thr Val Lys Ser Arg Trp Ser
    530                 535                 540

Gly Ser Gln Gln Val Glu Gln Pro Thr Gly Ser Val Leu Trp Met Ala
545                 550                 555                 560

Pro Glu Val Ile Arg Met Gln Asp Asn Asn Pro Phe Ser Phe Gln Ser
                565                 570                 575

Asp Val Tyr Ser Tyr Gly Ile Val Leu Tyr Glu Leu Met Thr Gly Glu
            580                 585                 590

Leu Pro Tyr Ser His Ile Asn Asn Arg Asp Gln Ile Ile Phe Met Val
        595                 600                 605

Gly Arg Gly Tyr Ala Ser Pro Asp Leu Ser Lys Leu Tyr Lys Asn Cys
    610                 615                 620

Pro Lys Ala Met Lys Arg Leu Val Ala Asp Cys Val Lys Lys Val Lys
625                 630                 635                 640

Glu Glu Arg Pro Leu Phe Pro Gln Ile Leu Ser Ser Ile Glu Leu Leu
                645                 650                 655
```

-continued

```
Gln His Ser Leu Pro Lys Ile Asn Arg Ser Ala Ser Glu Pro Ser Leu
            660                 665                 670

His Arg Ala Ala His Thr Glu Asp Ile Asn Ala Cys Thr Leu Thr Thr
        675                 680                 685

Ser Pro Arg Leu Pro Val Phe
    690                 695
```

RAF1 FUSIONS

CLAIM OF PRIORITY

This application is a national stage application of and claims priority under 35 USC § 371 to International Application No. PCT/US2015/035019, filed Jun. 10, 2015, which claims the benefit of U.S. Provisional No. 62/010,242, filed Jun. 10, 2014, the contents of both of which are incorporated herein by reference in their entirety to provide continuity of disclosure.

The instant application contains a Sequence Listing which has been submitted electronically in ASCII format and is hereby incorporated by reference in its entirety. Said ASCII copy, created on Jul. 21, 2015, is named 12386.0006-00304_SL.txt and is 62,795 bytes in size.

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer." *Nature* 444:561-566 (2007).

A need exists for identifying novel genetic lesions associated with cancer. For example, the presence of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients.

In one aspect, the invention provides methods for detecting the presence of a RAF1 fusion in a biological sample; the methods include the steps of: (a) obtaining a biological sample from a mammal; and (b) contacting the sample with a reagent that detects a RAF1 fusion, to determine whether a RAF1 fusion is present in the biological sample. In some embodiments, the sample can be from, e.g., a cancer patient. In some embodiments, the cancer is prostate adenocarcinoma. In some embodiments, the cancer is melanoma. In some embodiments, the fusion can be, e.g., an AGGF1:RAF1 fusion, an LMNA:RAF1 fusion, an MPRIP:RAF1 fusion, a PAPD7:RAF1 fusion, a CLCN6:RAF1 fusion, or a TRAK1:RAF1 fusion. In some embodiments, the AGGF1:RAF1 fusion has all or a part of the nucleotide and/or amino acid sequence (such as, e.g., the fusion junction) set forth in SEQ ID NO:1 and SEQ ID NO:2, respectively. In some embodiments, the LMNA:RAF1 fusion has all or part of the nucleotide and/or amino acid sequence (such as, e.g., the fusion junction) set forth in SEQ ID NO:3 and SEQ ID NO:4, respectively. In some embodiments, the MPRIP:RAF1 fusion has all or part of the nucleotide and/or amino acid sequence (such as, e.g., the fusion junction) set forth in SEQ ID NO:5 and SEQ ID NO:6, respectively. In some embodiments, the PAPD7:RAF1 fusion has all or part of the nucleotide and/or amino acid sequence (such as, e.g., the fusion junction) set forth in SEQ ID NO:7 and SEQ ID NO:8, respectively. In some embodiments, the CLCN6:RAF1 fusion has all or part of the nucleotide and/or amino acid sequence (such as, e.g., the fusion junction) set forth in SEQ ID NO:9 and SEQ ID NO:10, respectively. In some embodiments, the TRAK1:RAF1 fusion has all or part of the nucleotide and/or amino acid sequence (such as, e.g., the fusion junction) set forth in SEQ ID NO:11 and SEQ ID NO:12, respectively.

In another aspect, the invention provides methods of diagnosing a patient having a disease or disorder associated with aberrant RAF1 expression or activity, or overexpression of RAF1; the methods include: (a) obtaining a biological sample from the patient; and (b) contacting the sample with a reagent that detects a RAF1 fusion to determine whether a RAF1 fusion is present in the biological sample, wherein the detection of the RAF1 fusion indicates the presence of a disorder associated with aberrant RAF1 expression or activity, or overexpression of RAF1.

The invention also includes methods of determining a therapeutic regimen for treating a cancer in a human subject; methods of identifying a patient likely to respond to treatment with a RAF1 inhibitor or a RAF1 fusion inhibitor; methods of stratifying a patient population by detecting a RAF1 fusion; methods of treating a patient; methods of inhibiting the proliferation of cells containing a RAF1 fusion; methods of reducing an activity of a RAF1 fusion; methods of treating a condition mediated by aberrant RAF1 expression or activity; methods of treating a condition characterized by overexpression of RAF1; methods of identifying an agent that modulates the activity of a RAF1 fusion; and methods of monitoring disease burden in a patient having a condition mediated by RAF1.

BRIEF DESCRIPTION OF THE FIGURES

FIG. 1 depicts the nucleotide sequence of an AGGF1:RAF1 gene fusion (SEQ ID NO:1) comprising a portion of the AGGF1 gene (NM_018046) up to and including exon 5 (amino acid 290) and a portion of the RAF1 gene (NM_002880) starting at exon 8 (amino acid 279). The underlined codons at nucleotides 868-870 and 871-873 encode the last amino acid of AGGF1 and the first amino acid of RAF1, respectively. The slash after nucleotide 870 indicates the breakpoint (fusion junction) where translocation and in-frame fusion has occurred.

FIG. 2 depicts the amino acid sequence of an AGGF1:RAF1 fusion protein (SEQ ID NO:2). The slash between amino acids 290 and 291 indicates the breakpoint or fusion junction between the AGGF1 and RAF1 proteins. Amino acids 290-291 correspond to nucleotides 868-870 and 871-873 in SEQ ID NO:1.

FIG. 3 depicts the nucleotide sequence of an LMNA:RAF1 gene fusion (SEQ ID NO:3) comprising a portion of the LMNA gene (NM_170707) up to and including exon 10 (amino acid 566) and a portion of the RAF1 gene (NM_002880) starting at exon 8 (amino acid 279). The underlined codons at nucleotides 1696-1698 and 1699-1701 encode the last amino acid of LMNA and the first amino acid of RAF1, respectively. The slash after nucleotide 1698 indicates the breakpoint (fusion junction) where translocation and in-frame fusion has occurred.

FIG. 4 depicts the amino acid sequence of an LMNA: RAF1 fusion protein (SEQ ID NO:4). The slash between amino acids 566 and 567 indicates the breakpoint or fusion junction between the LMNA and RAF1 proteins. Amino acids 566-567 correspond to nucleotides 1696-1698 and 1699-1671 in SEQ ID NO:3.

FIGS. 5A & 5B depict the nucleotide sequence of an MPRIP:RAF1 gene fusion (SEQ ID NO:5) comprising an MPRIP gene (NM_201274) up to and including exon 22 (amino acid 1015) and a portion of the RAF1 gene (NM_002880) starting at exon 8 (amino acid 279). The underlined codons at nucleotides 3043-3045 and 3046-3048 encode the last amino acid of MPRIP and the first amino acid of RAF1, respectively. The slash between nucleotides 3045 and 3046 indicates the breakpoint or fusion junction where translocation and in-frame fusion has occurred.

FIG. 6 depicts the amino acid sequence of an MPRIP: RAF1 fusion protein (SEQ ID NO:6). The slash between amino acids 1015 and 1016 represents the location where the two proteins are fused and corresponds to nucleotides 3043-3045 and 3046-3048 of SEQ ID NO:5.

FIG. 7 depicts the nucleotide sequence of a PAPD7:RAF1 gene fusion (SEQ ID NO:7) comprising a PAPD7 gene (NM_006999) up to and including exon 11 (amino acid 423) and a portion of the RAF1 gene (NM_002880) starting at exon 10 (amino acid 331). The underlined codons at nucleotides 1267-1269 and 1270-1272 encode the last amino acid of PAPD7 and the first amino acid of RAF1, respectively. The slash between nucleotides 1269 and 1270 indicates the breakpoint or fusion junction where translocation and in-frame fusion has occurred.

FIG. 8 depicts the amino acid sequence of a PAPD7: RAF1 fusion protein (SEQ ID NO:8). The slash between amino acids 423 and 424 represents the location where the two proteins are fused and corresponds to nucleotides 1267-1269 and 1270-1272 of SEQ ID NO:7.

FIG. 9 depicts the nucleotide sequence of a CLCN6: RAF1 gene fusion (SEQ ID NO:9) comprising a CLCN6 gene (NM_001286) up to and including exon 2 (amino acid 49) and a portion of the RAF1 gene (NM_002880) starting at exon 8 (amino acid 279). The underlined codons at nucleotides 145-147 and 148-150 encode the last amino acid of CLCN6 and the first amino acid of RAF1, respectively. The slash between nucleotides 147 and 148 indicates the breakpoint or fusion junction where translocation and in-frame fusion has occurred.

FIG. 10 depicts the amino acid sequence of a CLCN6: RAF1 fusion protein (SEQ ID NO:10). The slash between amino acids 49 and 50 represents the location where the two proteins are fused and corresponds to nucleotides 145-147 and 148-150 of SEQ ID NO:9.

FIG. 11 depicts the nucleotide sequence of a TRAK1: RAF1 gene fusion (SEQ ID NO:11) comprising a TRAK1 gene (NM_001042646) up to and including exon 9 (amino acid 325) and a portion of the RAF1 gene (NM_002880) starting at exon 8 (amino acid 279). The underlined codons at nucleotides 973-975 and 976-978 encode the last amino acid of TRAK1 and the first amino acid of RAF1, respectively. The slash between nucleotides 975 and 976 indicates the breakpoint or fusion junction where translocation and in-frame fusion has occurred.

FIG. 12 depicts the amino acid sequence of an TRAK1: RAF1 fusion protein (SEQ ID NO:12). The slash between amino acids 325 and 326 represents the location where the two proteins are fused and corresponds to nucleotides 973-975 and 976-978 of SEQ ID NO:11.

EXEMPLARY EMBODIMENTS OF THE INVENTION

The invention is based, at least in part, on the discovery of novel recombination or translocation events in cancer patients that result in at least a fragment of a RAF1 gene linked to a non-homologous promoter via a recombination or translocation event that may result in aberrant expression (e.g., in a location where the kinase is not typically expressed) or overexpression of the kinase domain of the RAF1 gene and thus, an increase in kinase activity. Thus, a new patient population is identified, which is characterized by the presence of a RAF1 fusion, e.g., a RAF1 gene fusion or fusion protein. This new patient population suffers from or is susceptible to disorders mediated by aberrant RAF1 expression or activity, or overexpression of RAF1, such as, e.g., a cancer. In another aspect of the invention, a new subtype of cancer is identified, which is characterized by the presence of the RAF1 fusions described herein. In some embodiments, the new patient population suffers from or is susceptible to prostate adenocarcinoma or melanoma characterized by the presence of a RAF1 fusion. New methods of diagnosing and treating the patient population and the RAF1 fusion cancer subtype are also provided.

The term "RAF1 fusion" is used generically herein, and includes any fusion molecule (e.g., gene, gene product (e.g., cDNA, mRNA, or protein), and variants thereof) that includes a fragment of RAF1, particularly the coding region for the kinase domain of RAF1, and the coding region of a second, non-homologous gene and a promoter sequence from the non-homologous gene, such that the coding sequence for the kinase domain of RAF1 is under control of the promoter of the non-homologous gene. A RAF1 fusion protein generally includes the kinase domain of RAF1.

RAF1 Gene Fusions and Fusion Proteins

RAF1 is a member of the Raf kinase family of serine/threonine-specific protein kinases, from the TKL (Tyrosine-kinase-like) group of kinases. RAF1 is a MAP kinase (MAP3K) that can initiate the entire kinase cascade. Normal, cellular Raf genes have been shown to mutate to become oncogenes, by over stimulation of MEK1/2 and ERK1/2 activity.

RAF1 gene fusions are generated by a fusion between at least a part of the RAF1 gene and a part of another gene as a result of a translocation (including inversion) within a chromosome or between chromosomes. As a result of a translocation, the RAF11 gene may be placed under the transcriptional control of the partner gene promoter, resulting in aberrant RAF1 expression or activity, or overexpression of RAF1. The overexpression can lead to certain cancers. Alternatively or additionally, the partner gene may include a dimerization domain that causes RAF1 to become constitutively activated, or the fusion event may delete an autoregulatory region of RAF1 leading to a constitutively activated kinase. As used herein, the 5'-region is upstream of, and the 3'-region is downstream of, a fusion junction or breakpoint in one of the component genes. RAF1 and the gene or protein that it is fused to is referred to as "fusion partners." Alternatively, they may be identified as a "RAF1 gene fusion" or a "RAF1 fusion protein" which are collectively termed "RAF1 fusions." The RAF1 fusions disclosed herein have a kinase activity. The phrase "having a kinase activity" as used in this application means having an activity as an enzyme phosphorylating the side chain of an amino acid, such as serine or threonine.

In some exemplary embodiments, the fusion partner is all or a portion of AGGF1 (Angiogenic factor with G patch and FHA domains 1). In other exemplary embodiments, the fusion partner is all or a portion of LMNA (Lamin A/C). In other exemplary embodiments, the fusion partner is all or a portion of MPRIP (Myosin Phosphatase Rho Interacting Protein). In certain exemplary embodiments, the fusion partner is all or a portion of PAPD7 (PAP Associated Domain Containing 7). In other exemplary embodiments, the fusion partner is all or a portion of CLCN6 (chloride transport protein 6). In yet other exemplary embodiments, the fusion partner is all or a portion of TRAK1 (trafficking protein, kinesin binding 1).

Reference to "all or a portion" or "all or part" of a RAF1 gene fusion or SEQ ID NO:1, 3, 5, 7, 9, 11, or 13, means that the nucleotide sequence comprises the entire RAF1 gene fusion nucleotide sequence or a fragment of that sequence that comprises the fusion junction or breakpoint between RAF1 and its fusion partner (such as, e.g., AGGF1, LMNA, MPRIP, PAPD7, CLCN6, or TRAK1). The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spanning the fusion junction of the RAF1 gene fusion. Reference to "all or a portion" or "all or part" of a RAF1 fusion protein or SEQ ID NO:2, 4, 6, 8, 10, 12, or 14, means an amino acid sequence that comprises the entire RAF1 fusion protein amino acid sequence or a fragment of that sequence that comprises the fusion junction or breakpoint between RAF1 and its fusion partner (such as, e.g., AGGF1, LMNA, MPRIP, PAPD7, CLCN6, or TRAK1). The fragment may comprise 8, 10, 12, 14, 15, 16, 18, 20, 21, 22, 23, 24, 25, 26, 27, 28, 29, 30, 35, 40, 45, 50, 75, or more amino acids spanning the fusion junction.

In certain embodiments of the invention, a fusion includes an in-frame fusion of all or a portion of the AGGF1 gene (e.g., an AGGF1 promoter or a functional fragment thereof, and one or more exons encoding AGGF1 or a fragment thereof) and an exon of the RAF1 gene (e.g., one or more exons encoding a RAF1 kinase domain or a functional fragment thereof). Such a fusion can be referred to as an AGGF1:RAF11 fusion. In one embodiment, the AGGF1:RAF1 fusion comprises sufficient RAF1 sequence to drive expression of a fusion protein that has kinase activity, e.g., has elevated activity as compared with wild type RAF1 in the same tissue or cell.

In some embodiments, the invention provides an AGGF1:RAF1 gene fusion comprising the nucleotide sequence depicted in FIG. 1 (SEQ ID NO:1), or a fragment thereof that includes the fusion junction. SEQ ID NO:1 comprises AGGF1 (NM_018046) up to exon 5 (amino acid number 290) fused to RAF1 (NM_002880), beginning at exon 8 (amino acid number 279). In some embodiments the AGGF1:RAF1 gene fusion comprises a nucleotide sequence that is at least 85%, at least 90%, at least 95%, at least 97%, at least 98%, or at least 99% identical to all or part of SEQ ID NO:1. In some embodiments, the AGGF1:RAF1 gene fusion encodes a protein having the sequence depicted in FIG. 2 (SEQ ID NO:2) or a sequence that is at least 85%, at least 90%, at least 95%, at least 97%, at least 98%, or at least 99% identical to all or part of SEQ ID NO:2.

In other embodiments of the invention, a fusion includes an in-frame fusion of all or a portion of the LMNA gene (e.g., an LMNA promoter or a functional fragment thereof, and one or more exons encoding an LMNA or a fragment thereof) and an exon of the RAF1 gene (e.g., one or more exons encoding a RAF1 kinase domain or a functional fragment thereof). Such a fusion can be referred to as an LMNA:RAF1 fusion. In one embodiment, the LMNA:RAF1 fusion comprises sufficient RAF1 sequence to drive expression of a fusion protein that has kinase activity, e.g., has elevated activity as compared with wild type RAF1 in the same tissue or cell.

In some embodiments, the invention provides an LMNA:RAF1 gene fusion comprising the nucleotide sequence depicted in FIG. 3 (SEQ ID NO:3), or a fragment thereof that includes the fusion junction. SEQ ID NO:3 comprises LMNA (NM_170707) up to exon 10 (amino acid number 566) fused to RAF1 (NM_002880), beginning at exon 8 (amino acid number 279). In some embodiments the LMNA:RAF1 gene fusion comprises a nucleotide sequence that is at least 85%, at least 90%, at least 95%, at least 97%, at least 98%, or at least 99% identical to all or part of SEQ ID NO:3. In some embodiments, the LMNA:RAF1 gene fusion encodes a protein having the sequence depicted in FIG. 4 (SEQ ID NO:4) or a sequence that is at least 85%, at least 90%, at least 95%, at least 97%, at least 98%, or at least 99% identical to all or part of SEQ ID NO:4.

In certain embodiments of the invention, a fusion includes an in-frame fusion of all or a portion of the MPRIP gene (e.g., an MPRIP promoter or a functional fragment thereof, and one or more exons encoding an MPRIP or a fragment thereof) and an exon of the RAF1 gene (e.g., one or more exons encoding a RAF1 kinase domain or a functional fragment thereof). Such a fusion can be referred to as an MPRIP:RAF1 fusion. In some embodiments, the MPRIP:RAF1 fusion comprises sufficient RAF1 sequence to drive expression of a fusion protein that has kinase activity, e.g., has elevated activity as compared with wild type RAF1 in the same tissue or cell.

In other embodiments, the MPRIP:RAF1 fusion has the nucleotide sequence depicted in FIG. 5 (SEQ ID NO:5), or a fragment thereof that includes the fusion junction. SEQ ID NO:5 comprises MPRIP (NM_201274) up to and including exon 22 (amino acid number 1015) fused to RAF1 (NM_002880), beginning at exon 8 (amino acid 279). In some embodiments the MPRIP:RAF1 gene fusion comprises a nucleotide sequence that is at least 85%, at least 90%, at least 95%, at least 97%, at least 98%, or at least 99% identical to all or part of SEQ ID NO:5. In some embodiments, the MPRIP:RAF1 fusion encodes a protein having the sequence depicted in FIG. 6 (SEQ ID NO:6) or a sequence that is at least 85%, at least 90%, at least 95%, at least 97%, at least 98%, or at least 99% identical to all or part of SEQ ID NO:6.

In certain embodiments of the invention, a fusion includes an in-frame fusion of all or a portion of the PAPD7 gene (e.g., a PAPD7 promoter or a functional fragment thereof, and one or more exons encoding a PAPD7 or a fragment thereof) and an exon of the RAF1 gene (e.g., one or more exons encoding a RAF1 kinase domain or a functional fragment thereof). Such a fusion can be referred to as a PAPD7:RAF1 fusion. In one embodiment, the PAPD7:RAF1 fusion comprises sufficient RAF1 sequence to drive expression of a fusion protein that has kinase activity, e.g., has elevated activity as compared with wild type RAF1 in the same tissue or cell.

In some embodiments, the invention provides a PAPD7:RAF1 gene fusion comprising the nucleotide sequence depicted in FIG. 7 (SEQ ID NO:7), or a fragment of thereof that includes the fusion junction. SEQ ID NO:7 comprises PAPD7 (NM_006999) up to exon 11 (amino acid number 423) fused to RAF1 (NM_002880), beginning at exon 10 (amino acid number 331). In some embodiments the PAPD7:RAF1 gene fusion comprises a nucleotide sequence that is at least 85%, at least 90%, at least 95%, at least 97%, at least 98%, or at least 99% identical to all or part of SEQ ID NO:7. In some embodiments, the PAPD7:RAF1 gene fusion encodes a protein having the sequence depicted in FIG. 8 (SEQ ID NO:8) or a sequence that is at least 85%, at least 90%, at least 95%, at least 97%, at least 98%, or at least 99% identical to all or part of SEQ ID NO:8.

In certain embodiments of the invention, a fusion includes an in-frame fusion of all or a portion of the CLCN6 gene (e.g., a CLCN6 promoter or a functional fragment thereof, and one or more exons encoding a CLCN6 or a fragment thereof) and an exon of the RAF1 gene (e.g., one or more exons encoding a RAF11 kinase domain or a functional fragment thereof). Such a fusion can be referred to as a CLCN6:RAF1 fusion. In one embodiment, the CLCN6: RAF1 fusion comprises sufficient RAF1 sequence to drive expression of a fusion protein that has kinase activity, e.g., has elevated activity as compared with wild type RAF1 in the same tissue or cell.

In some embodiments, the invention provides a CLCN6: RAF1 gene fusion comprising the nucleotide sequence depicted in FIG. 9 (SEQ ID NO:9), or a fragment of thereof that includes the fusion junction. SEQ ID NO:9 comprises the CLCN6 gene (NM_001286) up to and including exon 2 fused to RAF1 (NM_002880), beginning at exon 8. In some embodiments the CLCN6:RAF1 gene fusion comprises a nucleotide sequence that is at least 85%, at least 90%, at least 95%, at least 97%, at least 98%, or at least 99% identical to all or part of SEQ ID NO:9. In some embodiments, the CLCN6:RAF1 gene fusion encodes a protein having the sequence depicted in FIG. 10 (SEQ ID NO:10) or a sequence that is at least 85%, at least 90%, at least 95%, at least 97%, at least 98%, or at least 99% identical to all or part of SEQ ID NO:10.

In certain embodiments of the invention, a fusion includes an in-frame fusion of all or a portion of the TRAK1 gene (e.g., a TRAK1 promoter or a functional fragment thereof, and one or more exons encoding a TRAK1 or a fragment thereof) and an exon of the RAF1 gene (e.g., one or more exons encoding a RAF1 kinase domain or a functional fragment thereof). Such a fusion can be referred to as a TRAK1:RAF1 fusion. In one embodiment, the TRAK1: RAF11 fusion comprises sufficient RAF1 sequence to drive expression of a fusion protein that has kinase activity, e.g., has elevated activity as compared with wild type RAF1 in the same tissue or cell.

In some embodiments, the invention provides a TRAK1: RAF1 gene fusion comprising the nucleotide sequence depicted in FIG. 11 (SEQ ID NO:11), or a fragment of thereof that includes the fusion junction. SEQ ID NO:11 comprises the TRAK1 gene (NM_001042646) up to and including exon 9 fused to RAF1 (NM_002880), beginning at exon 8. In some embodiments the TRAK1:RAF1 gene fusion comprises a nucleotide sequence that is at least 85%, at least 90%, at least 95%, at least 97%, at least 98%, or at least 99% identical to SEQ ID NO:11. In some embodiments, the TRAK:RAF1 gene fusion encodes a protein having the sequence depicted in FIG. 12 (SEQ ID NO:12) or a sequence that is at least 85%, at least 90%, at least 95%, at least 97%, at least 98%, or at least 99% identical to SEQ ID NO:12.

The nucleic acid sequences of RAF1 gene fusions may be used as probes, primers, or bait to identify nucleotides from a biological sample that include, flank, or hybridize to, RAF1 fusions, such as AGGF1:RAF1 (e.g., all or part of SEQ ID NO:1), LMNA:RAF1 (e.g., all or part of SEQ ID NO:3), MPRIP:RAF1 (e.g., all or part of SEQ ID NO:5), CLCN6:RAF1 (e.g., all or part of SEQ ID NO:9), or TRAK1:RAF1 (e.g., all or part of SEQ ID NO:11) at, e.g., the fusion junctions. In certain embodiments, the probe, primer, or bait molecule is an oligonucleotide that allows capture, detection, and/or isolation of a RAF1 gene fusion in a biological sample. In certain embodiments, the probes or primers derived from the nucleic acid sequences of RAF1 gene fusions (e.g., from the fusion junctions) may be used, for example, for polymerase chain reaction (PCR) amplification. The oligonucleotide can comprise a nucleotide sequence substantially complementary to a fragment of the RAF1 gene fusion nucleic acid molecules described herein. The sequence identity between the nucleic acid fragment, e.g., the oligonucleotide and the target RAF1 gene fusion sequence, need not be exact, so long as the sequences are sufficiently complementary to allow the capture, detection, and/or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of a RAF1 fusion, such as e.g., AGGF1: RAF1 (e.g., all or part of SEQ ID NO:1), LMNA:RAF1 (e.g., all or part of SEQ ID NO:3), MPRIP:RAF1 (e.g., all or part of SEQ ID NO:5), PAPD7:RAF1 (e.g., all or part of SEQ ID NO:7, CLCN6:RAF1 (e.g., all or part of SEQ ID NO:9), or TRAK1:RAF1 (e.g., all or part of SEQ ID NO:11). In other embodiments, the nucleic acid fragment is a bait that includes an oligonucleotide between about 100 to 300 nucleotides, 130 and 230 nucleotides, or 150 and 200 nucleotides in length that includes the fusion junction of a RAF1 fusion, such as e.g., AGGF1:RAF1 (e.g., all or part of SEQ ID NO:1), LMNA:RAF1 (e.g., all or part of SEQ ID NO:3). MPRIP:RAF1 (e.g., all or part of SEQ ID NO:5), PAPD7:RAF1 (e.g., all or part of SEQ ID NO:7), CLCN6: RAF1 (e.g., all or part of SEQ ID NO:9), or TRAK1:RAF1 (e.g., all or part of SEQ ID NO:11).

In certain embodiments, the nucleic acid fragments hybridize to a nucleotide sequence that includes a breakpoint or fusion junction, e.g., a breakpoint or fusion junction as identified by a slash ("/") in FIG. 1, 3, 5, 7, 9, or 11. For example, the nucleic acid fragment can hybridize to a nucleotide sequence that includes the fusion junction between the AGGF1 transcript and the RAF1 transcript (e.g., nucleotides 868-873 of SEQ ID NO:1), between the MPRIP transcript and the RAF1 transcript (e.g., nucleotides 1696-1701 of SEQ ID NO:3), between the LMNA transcript and the RAF1 transcript (e.g., nucleotides 3043-3048 of SEQ ID NO:5), between the PAPD7 transcript and the RAF1 transcript (e.g., nucleotides 1267-1272 of SEQ ID NO:7), between the CLCN6 transcript and the RAF1 transcript (e.g., nucleotides 145-150 of SEQ ID NO:9), or between the TRAK1 transcript and the RAF1 transcript (e.g., nucleotides 973-978 of SEQ ID NO:11), i.e., a nucleotide sequence that includes a portion of SEQ ID NO:1, 3, 5, 7, 9, or 11. Examples include a nucleotide sequence within exons 1 to 5 of an AGGF gene and exons 8-17 of a RAF1 gene (e.g., a portion of SEQ ID NO:1 comprising nucleotides 868-873, 866-875, 861-880, 846-895, or 821-920); a nucleotide sequence within exons 1-10 of an LMNA gene and exons 8 to 17 of a RAF1 gene (e.g., a portion of SEQ ID NO:3 comprising nucleotides 1696-1701, 1693-1702, 1688-1707, 1673-1722, or 1648-1747); a nucleotide sequence within exons 1-22 of an MPRIP gene and exons 8 to 17 of a RAF1 gene (e.g., a portion of SEQ ID NO:5 comprising nucleotides 3043-3048, 3041-3050, 3036-3055, 3021-3070, or 2996-3095); a nucleotide sequence within exons 1-11 of a PAPD7 gene and exons 10 to 17 of a RAF1 gene (e.g., a portion of SEQ ID NO:7 comprising nucleotides 1267-1272, 1265-1274, 1260-1279, 1245-1294); a nucleotide sequence within exons 1-2 of a CLCN6 gene and exons 8 to 17 of a RAF1 gene (e.g., a portion of SEQ ID NO:9 comprising nucleotides 145-150, 143-152, 138-157, 123-172, or 98-197); or a nucleotide sequence within exons 1-9 of a TRAK1 gene and exons 8 to 17 of a RAF1 gene (e.g., a portion of SEQ ID NO:11 comprising nucleotides 973-978, 971-980, 966-975, 951-990, or 926-1015).

In other embodiments, the nucleic acid fragment includes a bait that comprises a nucleotide sequence that hybridizes to a RAF1 gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments hybridize to a nucleotide sequence that includes a fusion junction between the AGGF1 transcript and the RAF1 transcript, e.g., a nucleotide sequence within SEQ ID NO:1 comprising nucleotides 868-873 (such as, e.g., a sequence comprising nucleotides 866-875, 861-880, 846-895, or 821-920 of SEQ ID NO:1).

In other exemplary embodiments, the nucleic acid fragments hybridize to a nucleotide sequence that includes a fusion junction between the LMNA transcript and the RAF1 transcript, e.g., a nucleotide sequence within SEQ ID NO:3 comprising nucleotides 1696-1701 (such as, e.g., a sequence comprising nucleotides 1693-1702, 1688-1707, 1673-1722, or 1648-1747 of SEQ ID NO:3).

In other exemplary embodiments, the nucleic acid fragments hybridize to a nucleotide sequence that includes a fusion junction between the MPRIP transcript and the RAF1 transcript, e.g., a nucleotide sequence within SEQ ID NO:5 comprising nucleotides 3043-3048 (such as, e.g., a sequence comprising nucleotides 3041-3050, 3036-3055, 3021-3070, or 2996-3095 of SEQ ID NO:5).

In other exemplary embodiments, the nucleic acid fragments hybridize to a nucleotide sequences that includes a fusion junction between the PAPD7 transcript and the RAF1 transcript, e.g., a nucleotide sequence within SEQ ID NO:7 comprising nucleotides 1267-1272 (such as, e.g., a sequence comprising nucleotides 1265-1274, 1260-1279, 1245-1294, or 1219-1318 of SEQ ID NO:7).

In some exemplary embodiments, the nucleic acid fragments hybridize to a nucleotide sequence that includes a fusion junction between the CLCN6 transcript and the RAF1 transcript, e.g., a nucleotide sequence within SEQ ID NO:9 comprising nucleotides 145-150 (such as, e.g., a sequence comprising nucleotides 143-152, 138-157, 123-172, or 98-197 of SEQ ID NO:9).

In other exemplary embodiments, the nucleic acid fragments hybridize to a nucleotide sequence that includes a fusion junction between the TRAK1 transcript and the RAF1 transcript, e.g., a nucleotide sequence within SEQ ID NO:11 comprising nucleotides 973-978 (such as, e.g., a sequence comprising nucleotides 971-980, 966-975, 951-990, or 926-1015 of SEQ ID NO:11).

Another aspect of the invention provides RAF1 fusion proteins (such as, e.g., a purified or isolated AGGF1:RAF1, LMNA:RAF11, MPRIP:RAF1, PAPD7:RAF1, CLCN6:RAF1, or TRAK1:RAF1 fusion protein), biologically active or antigenic fragments thereof, and use of those polypeptides for detecting and/or modulating the biological activity (such as tumorigenic activity) of a RAF1 fusion protein. Exemplary embodiments of the RAF1 fusion proteins comprise the amino acid sequence set forth in SEQ ID NO:2, 4, 6, 8, 10, or 12, and fragments of those sequences.

In some embodiments, the RAF1 fusion protein of the invention can include a fragment of an AGGF1 protein, an LMNA protein, an MPRIP protein, a PAPD7 protein, a CLCN6 protein, or a TRAK1 protein, and a fragment of a RAF1 protein. In one embodiment, the RAF1 fusion protein is AGGF1:RAF1 fusion protein having the amino acid sequence of SEQ ID NO:2 or a fragment thereof, such as, e.g., amino acids 286-295, 281-300, or 266-315 of SEQ ID NO:2. In other embodiments, the RAF1 fusion protein is an LMNA:RAF1 fusion protein having the amino acid sequence of SEQ ID NO:4 or a fragment thereof, such as, e.g., amino acids 562-572, 556-575, or 542-591 of SEQ ID NO:4. In some embodiments, the RAF1 fusion protein is an MPRIP:RAF1 fusion protein having the amino acid sequence of SEQ ID NO:6 or a fragment thereof, such as, e.g., amino acids 1011-1020, 1006-1025, or 991-1040 of SEQ ID NO:6. In other embodiments, the RAF1 fusion protein is a PAPD7:RAF1 fusion protein having the amino acid sequence of SEQ ID NO:8, or a fragment thereof, such as, e.g., amino acids 419-428, 414-433, or 399-448 of SEQ ID NO:8. In some embodiments, the RAF1 fusion protein is a CLCN6:RAF1 fusion protein having the amino acid sequence of SEQ ID NO:10 or a fragment thereof, such as, e.g., amino acids 45-54, 40-59, or 25-74 of SEQ ID NO:10. In other embodiments, the RAF1 fusion protein is a TRAK:RAF1 fusion protein having the amino acid sequence of SEQ ID NO:12 or a fragment thereof, such as, e.g., amino acids 321-330, 316-335, or 301-350 of SEQ ID NO:12.

In some embodiments, the RAF1 fusion protein is an AGGF1:RAF1 fusion protein comprising an amino acid sequence that is at least 85%, at least 90%, at least 95%, at least 97%, at least 98%, or at least 99% identical to SEQ ID NO:2 or a fragment thereof (e.g., amino acids 286-295, 281-300, or 266-315 of SEQ ID NO:2). In other embodiments, the RAF1 fusion protein is an LMNA:RAF1 fusion protein comprising an amino acid sequence that is at least 85%, at least 90%, at least 95%, at least 97%, at least 98%, or at least 99% identical to SEQ ID NO:4 or a fragment thereof (e.g., amino acids 562-572, 556-575, or 542-591 of SEQ ID NO:4). In yet other embodiments, the RAF1 fusion protein is an MPRIP:RAF1 fusion protein comprising an amino acid sequence that is at least 85%, at least 90%, at least 95%, at least 97%, at least 98%, or at least 99% identical to SEQ ID NO:6 or a fragment thereof (e.g., amino acids 1011-1020, 1006-1025, or 991-1040 of SEQ ID NO:6). In some embodiments the RAF1 fusion protein is a PAPD7:RAF1 fusion protein comprising an amino acid sequence that is at least 85%, at least 90%, at least 95%, at least 97%, at least 98%, or at least 99% identical to SEQ ID NO:8 or a fragment thereof (e.g., amino acids 419-428, 414-433, or 399-448 of SEQ ID NO:8). In some embodiments, the RAF1 fusion protein is a CLCN6:RAF1 fusion protein comprising an amino acid sequence that is at least 85%, at least 90%, at least 95%, at least 97%, at least 98%, or at least 99% identical to SEQ ID NO:10 or a fragment thereof (e.g., amino acids 45-54, 40-59, or 25-74 of SEQ ID NO:10). In other embodiments, the RAF1 fusion protein is a TRAK1:RAF1 fusion protein comprising an amino acid sequence that is at least 85%, at least 90%, at least 95%, at least 97%, at least 98%, or at least 99% identical to SEQ ID NO:12 or a fragment thereof (e.g., amino acids 321-330, 316-335, or 301-350 of SEQ ID NO:12).

In certain embodiments, the RAF1 fusion protein includes a functional kinase domain. In some embodiments, the RAF1 fusion protein comprises elevated RAF1 activity as compared with wild type RAF1 activity (e.g., in a cancer cell, a non-cancer cell adjacent to the cancer cell, or a non-cancer cell from a control sample, such as a cancer free subject). In one exemplary embodiment, the RAF1 fusion protein is an AGGF1:RAF1 fusion and includes a RAF1 serine/threonine kinase domain or a functional fragment thereof. In other exemplary embodiments, the RAF1 fusion protein is an LMNA:RAF1 fusion and includes a RAF1 serine/threonine kinase domain or a functional fragment thereof. In some exemplary embodiments, the RAF1 fusion protein is an MPRIP:RAF1 fusion and includes a RAF1 serine/threonine kinase domain or a functional fragment thereof. In yet other exemplary embodiments, the RAF1 fusion protein is a PAPD7:RAF1 fusion and includes a RAF1 serine/threonine kinase domain or a functional fragment thereof. In some exemplary embodiments, the RAF1 fusion protein is a CLCN6:RAF1 fusion and includes a RAF1 serine/threonine kinase domain or a functional fragment thereof. In other exemplary embodiments, the RAF1 fusion protein is a TRAK1:RAF1 fusion and includes a RAF1 serine/threonine kinase domain or a functional fragment thereof.

In another embodiment, the RAF1 fusion protein or fragment is a peptide, e.g., an immunogenic peptide or protein, that contains a fusion junction with a heterologous protein as described herein. Such immunogenic peptides or proteins can be used for vaccine preparation for use in the treatment or prevention of cancers caused by or exacerbated by RAF1 gene fusions and RAF1 fusion proteins. In other embodiments, such immunogenic peptides or proteins can be used to raise antibodies specific to the fusion protein. In some embodiments, the RAF1 fusion protein is present in combination with or is further conjugated to one or more adjuvant(s) or immunogen(s), e.g., a protein capable of enhancing an immune response to the RAF1 fusion protein (e.g., a hapten, a toxoid, etc.). In some embodiments, the RAF1 fusion protein is an AGGF1:RAF1, LMNA:RAF1, MPRIP:RAF1, PAPD7:RAF1, CLCN6:RAF1, or TRAK1:RAF1 fusion protein. In some embodiments, the RAF1 fusion protein comprises the fusion junction of SEQ ID NO:2, 4, 6, 8, 10, or 12.

Thus, another aspect of the invention provides an antibody that binds to a RAF1 fusion protein (such as, e.g., an AGGF1:RAF1, an LMNA:RAF1, an MPRIP:RAF1, a PAPD7:RAF1, a CLCN6:RAF1, or a TRAK1:RAF1 fusion protein) or a fragment thereof. In certain embodiments, the antibody recognizes a RAF1 fusion protein but does not recognize wild type RAF1 or the wild type fusion partner (such as, e.g., AGGF1, LMNA, MPRIP, PAPD7, CLCN6, or TRAK1). In some embodiments, the antibody binds to an epitope comprising the junction between RAF1 and the fusion partner (e.g., the junction of AGGF1:RAF1, LMNA:RAF1, MPRIP:RAF1. PAPD7:RAF1, CLCN6:RAF1, or TRAK1:RAF1). In one embodiment, the antibody binds to an AGGF1:RAF1 fusion protein having the amino acid sequence of SEQ ID NO:2 or a fragment thereof, such as, e.g., amino acids 286-295, 281-300, or 266-315 of SEQ ID NO:2. In other embodiments, the antibody binds to an LMNA:RAF1 fusion protein having the amino acid sequence of SEQ ID NO:4 or a fragment thereof, such as, e.g., amino acids 562-572, 556-575, or 542-591 of SEQ ID NO:4. In some embodiments, the antibody binds to an MPRIP:RAF1 fusion protein having the amino acid sequence of SEQ ID NO:6 or a fragment thereof, such as, e.g., amino acids 1011-1020, 1006-1025, or 991-1040 of SEQ ID NO:6. In other embodiments, the antibody binds to a PAPD7:RAF1 fusion protein having the amino acid sequence of SEQ ID NO:8 or a fragment thereof, such as, e.g., amino acids 419-428, 414-433, or 399-448 of SEQ ID NO:8. In other embodiments, the antibody binds to a CLCN6:RAF1 fusion protein having the amino acid sequence of SEQ ID NO:10 or a fragment thereof, such as, e.g., amino acids 45-54, 40-59, or 25-74 of SEQ ID NO:10. In yet other embodiments, the antibody binds to a TRAK1:RAF1 fusion protein having the amino acid sequence of SEQ ID NO:12 or a fragment thereof, such as, e.g., amino acids 321-330, 316-335, or 301-350 of SEQ ID NO:12.

In certain embodiments, the antibodies of the invention inhibit and/or neutralize the biological activity of the RAF1 fusion protein, and more specifically, in some embodiments, the kinase activity of the RAF1 fusion protein. In other embodiments, the antibodies may be used to detect a RAF1 fusion protein or to diagnose a patient suffering from a disease or disorder associated with the expression of a RAF1 fusion protein.

Detection and Diagnostic Methods

In another aspect, the invention provides a method of determining the presence of a RAF1 gene fusion or fusion protein, such as, e.g., an AGGF1:RAF1, an LMNA:RAF1, an MPRIP:RAF1, a PAPD7:RAF1, a CLCN6:RAF1, or a TRAK1:RAF1 fusion as described herein. The presence of a RAF1 fusion can indicate that the mammal providing the biological sample suffers from or is at risk of developing a disorder mediated by aberrant RAF1 expression or activity, or overexpression of RAF1, such as, e.g., a cancer. The presence of a RAF1 gene fusion may also indicate that the cancer is treatable with a RAF1 inhibitor (such as, e.g., a kinase inhibitor or an antibody specific to RAF1) or a RAF1 fusion inhibitor. In some embodiments, the RAF1 fusion present in the sample is AGGF1:RAF1 and the cancer to be treated is prostate adenocarcinoma. In other embodiments, the RAF1 fusion present in the sample is MPRIP:RAF1, LMNA:RAF1, CLCN6:RAF1, or TRAK1:RAF1 and the cancer to be treated is melanoma. In other embodiments, the cancer is a different cancer associated with aberrant expression or activity of RAF1 or overexpression of RAF1.

In one embodiment, the RAF1 fusion detected is a nucleic acid molecule or a polypeptide. The method includes detecting whether a RAF1 fusion nucleic acid molecule or polypeptide is present in a cell (e.g., a circulating cell or a cancer cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

The sample can be chosen from one or more sample types, such as, for example, tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

1. Methods for Detecting Gene Fusions

In some embodiments, the RAF1 fusion is detected in a nucleic acid molecule by one or more methods chosen from:

nucleic acid hybridization assays (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods).

(1) Hybridization Methods

In some embodiments, the reagent hybridizes to a RAF1 gene fusion, such as, e.g., nucleotides 868-873, 866-875, 861-880, 846-895, or 821-920 of SEQ ID NO:1. In alternate embodiments, the reagent detects the presence of nucleotides 1696-1701, 1693-1702, 1688-1707, 1673-1722, or 1648-1747 of SEQ ID NO:3, nucleotides 3043-3048, 3041-3050, 3036-3055, 3021-3070, or 2996-3095 of SEQ ID NO:5, nucleotides 1267-1272, 1265-1274, 1260-1279, 1245-1294, or 1219-1318 of SEQ ID NO:7, nucleotides 145-150, 143-152, 138-157, 123-172, or 98-197 of SEQ ID NO:9, or nucleotides 973-978, 971-980, 966-975, 951-990, or 926-1015 of SEQ ID NO:11.

In one embodiment, the method includes: contacting a nucleic acid sample, e.g., a genomic DNA sample (e.g., a chromosomal sample or a fractionated, enriched or otherwise pre-treated sample) or a gene product (mRNA, or cDNA), obtained from the subject, with a nucleic acid fragment e.g., a probe or primer as described herein (e.g., an exon-specific or a breakpoint-specific probe or primer) under conditions suitable for hybridization, and determining the presence or absence of the RAF1 gene fusion, such as, e.g. AGGF1:RAF1, LMNA:RAF1, MPRIP:RAF1, PAPD7:RAF1, CLCN6:RAF1, or TRAK1:RAF1, as described herein.

In an alternate embodiment, the method includes the steps of obtaining a sample; exposing the sample to a nucleic acid probe which hybridizes to an mRNA or cDNA encoding a RAF1 fusion protein that comprises amino acids 286-295, 281-300, or 266-315 of SEQ ID NO:2, amino acids 562-572, 556-575, or 542-591 of SEQ ID NO:4, amino acids 1011-1020, 1006-1025, or 991-1040 of SEQ ID NO:6, amino acids 419-428, 414-433, or 399-448 of SEQ ID NO:8, amino acids 45-54, 40-59, or 25-74 of SEQ ID NO:10, or amino acids 321-330, 316-335, or 301-350 of SEQ ID NO:12.

Hybridization, as described throughout the specification, may be carried out under stringent conditions, e.g., medium or high stringency. See, e.g., J. Sambrook, E. F. Fritsch, and T. Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2.10.16 (2001). High stringency conditions for hybridization refer to conditions under which two nucleic acids must possess a high degree of base pair homology to each other in order to hybridize. Examples of highly stringent conditions for hybridization include hybridization in 4× sodium chloride/sodium citrate (SSC), at 65 or 70° C., or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+BSA; ratio 1:1:1); 0.1% SDS; 5 mM EDTA; 50 mM $Na_2HPO_4$: 250 μg/ml of herring sperm DNA; 50 μg/ml of tRNA; or 0.25 M of sodium phosphate buffer, pH 7.2; 1 mM EDTA 7% SDS at 60° C.; followed by washing 2×SSC, 0.1% SDS at 60° C.

The nucleic acid fragments can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag, or identifier (e.g., an adaptor, barcode or other sequence identifier). Labeled or unlabeled nucleic acids and/or nucleic acid fragments may be used in reagents for detecting, capturing, or isolating RAF1 gene fusions. Labeled or unlabeled nucleic acids and/or nucleic acid fragments may be used in reagents for detecting, capturing, and/or isolating RAF1 gene fusions, such as, e.g., AGGF1:RAF1 (e.g., all or part of SEQ ID NO:1), LMNA:RAF1 (e.g., all or part of SEQ ID NO:3), MPRIP:RAF1 (e.g., all or part of SEQ ID NO:5), PAPD7:RAF1 (e.g., all or part of SEQ ID NO:7), CLCN6:RAF1 (e.g., all or part of SEQ ID NO:9), or TRAK1:RAF1 (e.g., all or part of SEQ ID NO:11). In some embodiments, the labeled reagent can be detected using, e.g., autoradiography, microscopy (e.g., brightfield, fluorescence, or electron microscopy), enzyme-linked immunosorbent assay (ELISA), or immunohistochemistry.

In some embodiments, the method comprises performing chromosome in situ hybridization with chromosomal DNA from a biological sample to detect the presence of a RAF1 gene fusion (such as, e.g., AGGF1:RAF1, LMNA:RAF1, MPRIP:RAF1, PAPD7:RAF1, CLCN6:RAF1, or TRAK1:RAF1, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of a RAF1 gene fusion (such as, e.g., AGGF1:RAF1, LMNA:RAF1, MPRIP:RAF1, PAPD7:RAF1, CLCN6:RAF1, or TRAK1:RAF1, as disclosed herein). In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

(2) Amplification-Based Assays

In certain embodiments, the method of determining the presence of a RAF1 gene fusion, comprises (a) performing a PCR amplification reaction with polynucleotides from a biological sample, wherein the amplification reaction utilizes a pair of primers which will amplify at least a fragment of the RAF1 gene fusion, wherein the fragment comprises the fusion junction, wherein the first primer is in sense orientation and the second primer is in antisense orientation; and (b) detecting an amplification product, wherein the presence of the amplification product is indicative of the presence of a RAF1 fusion polynucleotide in the sample. In specific exemplary embodiments, the RAF1 gene fusion is AGGF1:RAF1, such as, e.g., the gene fusion of SEQ ID NO:1 or a fragment thereof comprising nucleotides 868-873, 866-875, 861-880, 846-895, or 821-920 of SEQ ID NO:1 In other exemplary embodiments, the gene fusion is LMNA:RAF1 such as, e.g. the gene fusion of SEQ ID NO:3 or a fragment thereof comprising nucleotides 1696-1701, 1693-1702, 1688-1707, 1673-1722, or 1648-1747 of SEQ ID NO:3. In other exemplary embodiments, the gene fusion is MPRIP:RAF1 such as, e.g. the gene fusion of SEQ ID NO:5 or a fragment thereof comprising nucleotides 3043-3048, 3041-3050, 3036-3055, 3021-3070, or 2996-3095 of SEQ ID NO:5. In certain exemplary embodiments, the gene fusion is PAPD7:RAF1 such as, e.g. the gene fusion of SEQ ID NO:7 or a fragment thereof comprising nucleotides 1267-1272, 1265-1274, 1260-1279, 1245-1294, or 1219-1318 of SEQ ID NO:7. In some exemplary embodiments, the gene fusion is CLCN6:RAF1 such as, e.g. the gene fusion of SEQ ID NO:9 or a fragment thereof comprising nucleotides 145-150, 143-152, 138-157, 123-172, or 98-197 of SEQ ID NO:9. In other exemplary embodiments, the gene fusion is TRAK1:RAF1 such as, e.g. the gene fusion of SEQ ID NO:11 or a fragment thereof comprising nucleotides 973-978, 971-980, 966-975, 951-990, or 926-1015 of SEQ ID NO:11.

In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the RAF1 gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles).

In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

(3) Sequencing and Genotyping

Another method for determining the presence of a RAF1 gene fusion molecule (such as, e.g., AGGF1:RAF1, LMNA:RAF1, MPRIP:RAF1, PAPD7:RAF1, CLCN6:RAF1, or TRAK1:RAF1, as disclosed herein) includes: sequencing a portion of the nucleic acid molecule (e.g., sequencing the portion of the nucleic acid molecule that comprises the fusion junction of a RAF1 gene fusion), thereby determining that the RAF1 gene fusion is present in the nucleic acid molecule. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule: (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme: (v) generating a detectable signal by the second enzyme using the ATP; (vi) detecting the generated signal and analyzing the amount of signal generated in a pyrogram; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of a RAF1 fusion (such as, e.g., AGGF1:RAF1, LMNA:RAF1. MPRIP:RAF1, PAPD7:RAF1, CLCN6: RAF1, or TRAK1:RAF1 as disclosed herein) comprises analyzing a nucleic acid sample (e.g., DNA, cDNA, or RNA, or an amplification product thereof) by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffininity HPLC.

In some embodiments, the method of determining the presence of a RAF1 fusion (such as, e.g., AGGF1:RAF1, LMNA:RAF1, MPRIP:RAF1, PAPD7:RAF1, CLCN6: RAF1, or TRAK1:RAF1, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

II. Methods for Detecting Fusion Proteins

Another aspect of the invention provides a method of determining the presence of a RAF1 fusion protein in a mammal. The method comprises the steps of obtaining a biological sample of a mammal (such as, e.g., a human cancer), and exposing that sample to at least one reagent that detects a RAF1 fusion protein (e.g., an antibody that recognizes the RAF1 fusion but does not recognize the wild type RAF1 or the wild type fusion partner) to determine whether a RAF1 fusion protein is present in the biological sample. The detection of a RAF1 fusion protein indicates the presence of a mutant RAF1 in the mammal (such as, e.g., in the human cancer). In some embodiments, the RAF1 fusion protein comprises an amino acid sequence having at least 85%, 90%, 95%, 97%, 98%, or 99% identity with an amino acid sequence of all or part of SEQ ID NO:2, 4, 6, 8, 10, or 12. In some embodiments the cancer is melanoma. In some embodiments, the cancer is prostate adenocarcinoma.

In some embodiments, the reagent that detects a RAF1 fusion protein can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, barcode or other sequence identifier). In some embodiments, the labeled reagent can be detected using, e.g., autoradiography, microscopy (e.g., brightfield, fluorescence, or electron microscopy), ELISA, or immunohistochemistry. In some embodiments, the RAF1 fusion protein is detected in a biological sample by a method chosen from one or more of: antibody-based detection (e.g., western blot, ELISA, immunohistochemistry), size-based detection methods (e.g., HPLC or mass spectrometry), or protein sequencing.

(1) Antibody-Based Detection

In some embodiments, the method comprises performing a western blot with polypeptides from a biological sample to detect the presence of a RAF1 fusion protein (such as, e.g., AGGF1:RAF1, LMNA:RAF1, MPRIP:RAF1. PAPD7: RAF1, CLCN6:RAF1, or TRAK1:RAF1, as disclosed herein). In some embodiments, the western blot comprises the steps of: separating the polypeptides by gel electrophoresis; transferring the polypeptides from the gel to a membrane (e.g., a nitrocellulose or polyvinylidene difluoride (PVDF) membrane); blocking the membrane to prevent nonspecific binding by incubating the membrane in a dilute solution of protein (e.g., 3-5% bovine serum albumin (BSA) or non-fat dry milk in Tris-Buffered Saline (TBS) or I-Block, with a minute percentage (e.g., 0.1%) of detergent, such as, e.g., Tween 20 or Triton X-100); exposing the polypeptides to at least one reagent that detects a RAF1 fusion protein (e.g., an antibody that recognizes the RAF1 fusion but does not recognize the wild type RAF1 or the wild type fusion partner); removing unbound or non-specifically bound reagent by washing; and detecting the binding of the reagent with the target protein. In some embodiments, the method comprises two-step detection: exposing the polypeptides to a primary antibody that specifically binds to a RAF1 fusion protein; removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the reagent that detects a RAF1 fusion protein (e.g., the fusion specific antibody, or the secondary antibody) is directly labeled for detection. In other embodiments, the reagent is linked to an enzyme, and the method further comprises adding a substrate of the enzyme to the membrane; and developing the membrane by detecting a detectable signal produced by the reaction between the enzyme and the substrate. For example, the reagent may be linked with horseradish peroxidase to cleave a chemiluminescent agent as a substrate, producing luminescence in proportion to the amount of the target protein for detection.

In some embodiments, the method comprises performing ELISA with polypeptides from a biological sample to detect the presence of a RAF1 fusion protein (such as, e.g., AGGF:RAF1, LMNA:RAF1, MPRIP:RAF1, PAPD7: RAF1, CLCN6:RAF1, or TRAK1:RAF1, as disclosed herein). In some embodiments, the ELISA is chosen from, e.g., direct ELISA, indirect ELISA, sandwich ELISA, and competitive ELISA.

In one embodiment, the direct ELISA comprises the steps of: attaching polypeptides from a biological sample to a surface; blocking the surface to prevent nonspecific binding by incubating the surface in a dilute solution of protein; exposing the polypeptides to an antibody that specifically binds to a RAF1 fusion protein (e.g., an antibody that recognizes the RAF1 fusion (such as, e.g., AGGF1:RAF1, LMNA:RAF1, MPRIP:RAF1, PAPD7:RAF1, CLCN6: RAF1, or TRAK1:RAF1, as disclosed herein) but does not recognize the wild type RAF1 or the wild type fusion partner); removing unbound or non-specifically bound antibody by washing; and detecting the binding of the antibody with the target protein. In some embodiments, the antibody is directly labeled for detection. In other embodiments, the antibody is linked to an enzyme, and the method further comprises adding a substrate of the enzyme; and detecting a detectable signal produced by the reaction between the enzyme and the substrate.

In another embodiment, the indirect ELISA comprises the steps of: attaching polypeptides from a biological sample to a surface; blocking the surface to prevent nonspecific binding by incubating the surface in a dilute solution of protein; exposing the polypeptides to a primary antibody that specifically binds to a RAF1 fusion protein (such as, e.g., AGGF1:RAF1, LMNA:RAF1, MPRIP:RAF1, PAPD7:RAF1, CLCN6:RAF1, or TRAK1:RAF1, as disclosed herein); removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the secondary antibody is directly labeled for detection. In other embodiments, the secondary antibody is linked to an enzyme, and the method further comprises adding a substrate of the enzyme; and detecting a detectable signal produced by the reaction between the enzyme and the substrate.

In some embodiments, the method comprises performing immunohistochemistry with polypeptides from a biological sample to detect the presence of a RAF1 fusion protein (such as, e.g., AGGF1:RAF1, LMNA:RAF1, MPRIP:RAF1, PAPD7:RAF1, CLCN6:RAF1, or TRAK1:RAF1, as disclosed herein). In some embodiments, the immunohistochemistry comprises the steps of: fixing a cell or a tissue section (e.g., by paraformaldehyde or formalin treatment); permeabilizing the cell or tissue section to allow target accessibility; blocking the cell or tissue section to prevent nonspecific binding; exposing the cell or tissue section to at least one reagent that detects a RAF1 fusion protein (e.g., an antibody that recognizes the RAF1 fusion but does not recognize the wild type RAF1 or the wild type fusion partner); removing unbound or non-specifically bound reagent by washing; and detecting the binding of the reagent with the target protein. In some embodiments, the reagent is directly labeled for detection. In other embodiments, the reagent is linked to an enzyme, and the method further comprises adding a substrate of the enzyme; and detecting a detectable signal produced by the reaction between the enzyme and the substrate. In some embodiments, the immunohistochemistry may comprise the two-step detection as in the indirect ELISA.

(2) Size-Based Detection Methods

In some embodiments, the method of determining the presence of a RAF1 fusion (such as, e.g., AGGF1:RAF1, LMNA:RAF1, MPRIP:RAF1, PAPD7:RAF1, CLCN6:RAF1, or TRAK1:RAF1, as disclosed herein) comprises analyzing a protein sample by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a RAF1 fusion (such as, e.g., AGGF1:RAF1, LMNA:RAF1, MPRIP:RAF1, PAPD7:RAF1, CLCN6:RAF1, or TRAK1:RAF1, as disclosed herein) comprises analyzing a protein sample by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of a RAF1 gene fusion or a RAF1 fusion protein in a patient can lead to assignment of the patient to the newly identified patient population that bears the RAF1 fusion. Because this patient population can suffer from or be susceptible to a disorder associated with aberrant RAF1 expression or activity or overexpression of RAF1, detection of the RAF1 fusion can also lead to diagnosis of such disorder. Thus, a further aspect of the invention provides a method of stratifying a patient population (e.g., assigning a patient, to a group or class) and/or diagnosing a patient, comprising: obtaining a biological sample from the patient, contacting the sample with at least one reagent that detects a RAF1 gene fusion or a RAF1 fusion protein to determine whether a RAF1 fusion is present in the biological sample. The detection of a RAF1 fusion indicates that the patient belongs to the newly identified patient population that bears the RAF1 fusion, and/or the presence of a disorder associated with aberrant RAF1 expression or activity or overexpression of RAF1, such as e.g., a cancer. The detection of a RAF1 fusion also identifies a new subtype of cancer, which is characterized by the presence of the RAF1 fusion. In some embodiments, the cancer is melanoma. In some embodiments, the cancer is prostate adenocarcinoma. In certain embodiments, the RAF1 fusion is AGGF1:RAF1. In other embodiments, the RAF1 fusion is LMNA:RAF11, MPRIP:RAF1, PAPD7:RAF11, CLCN6:RAF1, or TRAK1:RAF1. In some embodiments, the AGGF1:RAF1 fusion has all or a part of the nucleotide and/or amino acid sequence (such as, e.g., the fusion junction) set forth in SEQ ID NO:1 and SEQ ID NO:2, respectively. In some embodiments, the LMNA:RAF1 fusion has all or part of the nucleotide and/or amino acid sequence (such as, e.g., the fusion junction) set forth in SEQ ID NO:3 and SEQ ID NO:4, respectively. In some embodiments, the MPRIP:RAF1 fusion has all or part of the nucleotide and/or amino acid sequence (such as, e.g., the fusion junction) set forth in SEQ ID NO:5 and SEQ ID NO:6, respectively. In some embodiments, the PAPD7:RAF1 fusion has all or part of the nucleotide and/or amino acid sequence (such as e.g., the fusion junction) set forth in SEQ ID NO:7 and SEQ ID NO:8, respectively. In some embodiments, the CLCN6:RAF1 fusion has all or part of the nucleotide and/or amino acid sequence (such as, e.g., the fusion junction) set forth in SEQ ID NO:9 and SEQ ID NO:10, respectively. In some embodiments, the TRAK1:RAF1 fusion has all or part of the nucleotide and/or amino acid sequence (such as, e.g., the fusion junction) set forth in SEQ ID NO:11 and SEQ ID NO:12, respectively.

In some embodiments, the RAF1 gene fusion or RAF1 fusion protein is detected prior to initiating, during, and/or after, a treatment of a patient with, e.g., a RAF1 inhibitor or a RAF1 fusion inhibitor. In one embodiment, the RAF1 gene fusion or RAF1 fusion protein is detected at the time the patient is diagnosed with a cancer. In other embodiment, the RAF1 fusion is detected at a pre-determined interval, e.g., a first point in time and at least at a subsequent point in time. In certain embodiments, in response to detection of a RAF1 fusion, such as, e.g., AGGF1:RAF1, LMNA:RAF1, MPRIP:RAF1, PAPD7:RAF1, CLCN6:RAF1, or TRAK:RAF1, the method further includes one or more of:

(1) stratifying a patient population (e.g., assigning a patient, to a group or class);

(2) identifying or selecting the patient as likely or unlikely to respond to a treatment, e.g., a RAF1 inhibitor treatment (e.g., a kinase inhibitor treatment), or a RAF1 fusion inhibitor treatment as described herein;

(3) selecting a treatment regimen, e.g., administering or not administering a preselected therapeutic agent, such as, e.g., a RAF1 inhibitor, or a RAF1 fusion inhibitor;

(4) prognosticating the time course of the disease in the patient (e.g., evaluating the likelihood of increased or decreased patient survival); or (5) monitoring the effectiveness of treatment (e.g., by detecting a reduction in the level of RAF1 gene fusion or fusion protein in a patient sample).

In certain embodiments, upon detection of a RAF1 gene fusion or RAF1 fusion protein in a patient's biological sample, the patient is identified as likely to respond to a treatment that comprises a RAF1 inhibitor, or a RAF1 fusion inhibitor. In some embodiments, the RAF1 fusion detected is an AGGF1:RAF1 fusion. In alternate embodiments, the RAF1 fusion detected is an MPRIP:RAF1 fusion. In some embodiments, the RAF1 fusion detected is a PAPD7:RAF1 fusion. In some embodiments, the RAF1 fusion detected is a LMNA:RAF1 fusion. In some embodiments, the RAF1 fusion detected is a CLCN6:RAF1 fusion. In some embodiments, the RAF1 fusion detected is a TRAK1:RAF1 fusion.

A further aspect of the invention provides a method of selecting a treatment option by detecting a RAF1 fusion. The method comprises obtaining a biological sample from a patient and exposing the sample to at least one reagent that detects a RAF1 gene fusion or fusion protein to determine whether a RAF1 fusion is present in the biological sample. The detection of the RAF1 fusion indicates the likelihood of the patient responding to treatment with a RAF1 inhibitor, or a RAF1 fusion inhibitor. The method may be augmented or personalized by evaluating the effect of a variety of kinase, RAF1 or RAF1 fusion inhibitors on the biological sample shown to contain a RAF1 fusion to determine the most appropriate inhibitor to administer. In certain embodiments, the RAF1 fusion is AGGF1:RAF1. In other embodiments, the RAF1 fusion is LMNA:RAF1, MPRIP:RAF1, PAPD7:RAF1, CLCN6:RAF1, or TRAK1:RAF1. In some embodiments, the AGGF1:RAF1 fusion has all or a part of the nucleotide and/or amino acid sequence (such as, e.g., the fusion junction) set forth in SEQ ID NO:1 and SEQ ID NO:2, respectively. In some embodiments, the LMNA:RAF1 fusion has all or part of the nucleotide and/or amino acid sequence (such as, e.g., the fusion junction) set forth in SEQ ID NO:3 and SEQ ID NO:4, respectively. In some embodiments, the MPRIP:RAF1 fusion has all or part of the nucleotide and/or amino acid sequence (such as, e.g., the fusion junction) set forth in SEQ ID NO:5 and SEQ ID NO:6, respectively. In some embodiments, the PAPD7:RAF1 fusion has all or part of the nucleotide and/or amino acid sequence (such as, e.g., the fusion junction) set forth in SEQ ID NO:7 and SEQ ID NO:8, respectively. In some embodiments, the CLCN6:RAF1 fusion has all or part of the nucleotide and/or amino acid sequence (such as, e.g., the fusion junction) set forth in SEQ ID NO:10 and SEQ ID NO:11, respectively. In some embodiments, the TRAK1:RAF1 fusion has all or part of the nucleotide and/or amino acid sequence (such as, e.g., the fusion junction) set forth in SEQ ID NO:11 and SEQ ID NO:12, respectively.

Methods of Treatment

Alternatively, or in combination with the detection and diagnostic methods described herein, the invention provides method for treating the newly identified patient population and the new RAF1 fusion cancer subtype, which are characterized by the presence of a RAF1 fusion. The patient population and cancer subtype can be associated with or predict the onset of a condition mediated by aberrant RAF1 expression or activity, or overexpression of RAF1, such as, e.g., a cancer or a tumor harboring a RAF1 fusion. The methods comprise administering a therapeutic agent, e.g., a RAF1 inhibitor, such as e.g., a kinase inhibitor or an antibody specific to RAF1; or a RAF1 fusion inhibitor, i.e., an inhibitor that blocks the activity of the RAF1 fusion but not wild type RAF1 or wild type fusion partner, such as e.g., an antibody specific to an AGGF1:RAF1, an LMNA:RAF1, an MPRIP:RAF1, a PAPD7:RAF1, a CLCN6:RAF1, or a TRAK1:RAF1 fusion protein, e.g., any one of the antibodies described above, or an RNA inhibitor that recognizes RAF1 or the fusion junction of a RAF1 gene fusion, including but not limited to siRNA, dsRNA, shRNA, or any other antisense nucleic acid inhibitor, alone or in combination with e.g., other chemotherapeutic agents or procedures, in an amount sufficient to treat a condition mediated by aberrant RAF1 expression or activity, or overexpression of RAF1 by one or more of the following: impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

In certain embodiments, the RAF1 fusion of the invention may be inhibited by a RAF1 inhibitor or a RAF1 fusion inhibitor. In some embodiments, the therapeutic agent is a RAF1 inhibitor, such as, e.g., a compound, biological or chemical, which inhibits, directly or indirectly, the expression and/or activity of RAF1. For example, the RAF1 inhibitors may be an antibody (such as, e.g., antibodies specific to RAF1) or a small molecule inhibitor (such as, e.g., a kinase inhibitor). In some embodiments, the inhibitors may act directly on RAF1 itself, modify the activity of RAF1, or inhibit the expression of RAF1. In other embodiments, the inhibitors may indirectly inhibit RAF1 activity by inhibiting the activity of proteins or molecules other than RAF1 itself. For example, the inhibitors may modulate the activity of regulatory kinases that phosphorylate or dephosphorylate RAF1, interfere with binding of ligands, or inhibit the activity of interacting or downstream proteins or molecules.

In some embodiments, the RAF1 fusion is inhibited by a RAF1 fusion inhibitor, such as, e.g., an antibody that recognizes all or part of a RAF1 fusion (such as, e.g., AGGF1:RAF1, LMNA:RAF1, MPRIP:RAF1, PAPD7:RAF1, CLCN6:RAF1, or TRAK1:RAF1, as described herein) but does not recognize wild type RAF1 or wild type fusion partner (e.g., AGGF1, LMNA, MPRIP, PAPD7, CLCN6, or TRAK1). In some embodiments, the RAF1 fusion protein (such as, e.g., AGGF1:RAF1, LMNA:RAF1, MPRIP:RAF1, PAPD7:RAF1, CLCN6:RAF1, or TRAK1:RAF1, as described herein) is inhibited by an agent that inhibits transcription or translation of the fusion protein, e.g., an RNA inhibitor that recognizes the RAF1 coding sequence, the binding partner (e.g., AGGF1, LMNA, MPRIP, PAPD7, CLCN6, or TRAK1), or the binding partner: RAF1 fusion junction, including but not limited to small interfering RNA (siRNA), double stranded RNA (dsRNA), short-hairpin RNA (shRNA), or any other antisense nucleic acid inhibitor.

In some embodiments, the RAF1 fusion inhibited is selected from all or a portion of any one of SEQ ID NOs: 1-12.

As used herein, and unless otherwise specified, a "therapeutically effective amount" of a compound is an amount sufficient to provide a therapeutic benefit in the treatment or management of a condition mediated by aberrant RAF1 expression or activity, or overexpression of RAF1, such as, delaying or minimizing one or more symptoms associated with a cancer or a tumor harboring a RAF1 fusion (such as, e.g., AGGF1:RAF1, LMNA:RAF1, MPRIP:RAF1, PAPD7:RAF1, CLCN6:RAF1, or TRAK1:RAF1, as described herein). A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the condition mediated by aberrant RAF1 expression activity or overexpression of RAF1, or enhances the therapeutic efficacy of another therapeutic agent.

In certain embodiments, the cancer or tumor harboring a RAF1 fusion is melanoma. In some embodiments the cancer or tumor harboring a RAF1 fusion is a prostate adenocarcinoma.

In some embodiments, the patient to be treated is suffering from melanoma, and the method for treating the condition comprises administering to the patient a therapeutically effective amount of a RAF1 inhibitor or a RAF1 fusion inhibitor as described above. In some embodiments, the patient to be treated is suffering from prostate adenocarcinoma, and the method for treating the condition comprises administering to the patient a therapeutically effective amount of a RAF1 inhibitor or a RAF1 fusion inhibitor as described above.

Screening Methods

Therapeutic agents, such as, e.g., RAF1 inhibitors, and RAF1 fusion inhibitors (gene fusion and fusion protein), used in the therapeutic methods of the invention can be evaluated using the screening assays described herein. Thus, the invention provides a method of identifying an agent useful for treating a condition mediated by aberrant RAF1 expression or activity, or overexpression of RAF1, e.g., cancer or a tumor harboring a RAF1 fusion, such as, e.g., melanoma or prostate adenocarcinoma, comprising contacting a cell expressing a RAF1 gene fusion or RAF1 fusion protein with a candidate agent and using one of the detection methods referenced above to determine whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing a RAF1 fusion (e.g., a mammalian cell, a tumor cell or cell line, a recombinant cell). In yet other embodiments, the therapeutic agents are evaluated in a cell in vivo (a RAF1 fusion-expressing cell present in a subject, e.g., an animal subject (e.g., an in vivo animal model).

Exemplary parameters to evaluate in determining the efficacy of a therapeutic agent for treating a condition mediated by aberrant RAF1 expression or activity, or overexpression of RAF1, such as, e.g., a cancer or a tumor harboring a RAF1 fusion include one or more of:

(i) a change in binding activity, e.g., direct binding of the candidate agent to a RAF1 fusion protein or a binding competition between a known ligand and the candidate agent to a RAF1 fusion protein;

(ii) a change in kinase activity, e.g., phosphorylation levels of a RAF1 fusion protein (e.g., an increased or decreased phosphorylation or autophosphorylation) or a change in phosphorylation of a target of a RAF1 kinase—in certain embodiments, a change in kinase activity, e.g., phosphorylation, is detected by any of western blot (e.g., using an anti-RAF1 antibody or a phosphor-specific antibody, detecting a shift in the molecular weight of a RAF1 fusion protein), mass spectrometry, immunoprecipitation, immunohistochemistry, immunomagnetic beads, among others;

(iii) a change in an activity of a cell containing a RAF1 fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor;

(v) a change in the level, e.g., expression level, of a RAF1 fusion protein or nucleic acid molecule; or (vi) a change in an activity of a signaling pathway involving RAF1, e.g., phosphorylation or activity of an interacting or downstream target, or expression level of a target gene.

In some embodiments, the RAF1 fusion is an AGGF1:RAF1 fusion, an LMNA:RAF1 fusion, an MPRIP:RAF1 fusion, a PAPD7:RAF1 fusion, a CLCN6:RAF1 fusion, or a TRAK1:RAF1 fusion.

In one embodiment, a change in the activity of a RAF1 fusion, or interaction of a RAF1 fusion with a downstream ligand detected in a cell free assay in the presence of a candidate agent indicates that the candidate agent will be effective as a therapeutic agent for treatment of a condition mediated by aberrant RAF1 expression or activity, or overexpression of RAF1, such as, e.g., a cancer or a tumor harboring a RAF1 fusion. In some embodiments, the cancer or tumor is postate adenocarinoma. In some embodiments, the cancer or tumor is melanoma.

In other embodiments, a change in an activity of a cell expressing a RAF1 fusion, such as, e.g., AGGF1:RAF1, LMNA:RAF1, MPRIP:RAF1, PAPD7:RAF1, CLCN6:RAF1, or TRAK1:RAF1, as described herein, (e.g., a mammalian cell, a tumor cell or cell line, a recombinant cell) is detected in a cell in culture. In one embodiment, the cell is a recombinant cell that is modified to express a RAF1 fusion nucleic acid, e.g., is a recombinant cell transfected with a RAF1 fusion nucleic acid. The transfected cell can show a change in response to the expressed RAF1 fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, or transformed morphology, in the presence of the candidate agent can be indicative of an inhibitor of a RAF1 fusion. In other embodiments, a change in binding activity or phosphorylation of RAF1 or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing a RAF1 fusion (e.g., tumorigenic cells expressing a RAF1 fusion) is employed. The therapeutic agents can be administered to the animal subject and a change in the tumor is evaluated. In one embodiment, the change in the tumor includes one or more of a tumor growth, tumor size, tumor burden, or survival is evaluated. A decrease in one or more of tumor growth, tumor size, tumor burden, or an increased survival is indicative that the candidate agent is an inhibitor or modulator.

In another aspect of the invention provides a method or assay for screening for agents that modulate (e.g., inhibit) the expression or activity of a RAF1 fusion as described herein. The method includes contacting e.g., a RAF1 fusion, or a cell expressing a RAF1 fusion, with a candidate agent; and detecting a change in a parameter associated with a RAF1 fusion, e.g., a change in the expression or an activity of the RAF1 fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the RAF1 fusion is detected, the candidate agent is identified as an inhibitor. In another embodiment, if an increase in expression or activity of the RAF1 fusion is detected, the candidate agent is identified as an activator. In certain embodiments, the RAF1 fusion is a RAF1 gene fusion or RAF1 fusion protein, such as, e.g., an AGGF1:RAF1 fusion, an MPRIP:RAF1 fusion, a PAPD7:RAF1 fusion, an LMNA:RAF1 fusion, a CLCN6:RAF1 fusion, or a TRAK1:RAF1 fusion.

In one embodiment, the contacting step is detected in a cell-free system, e.g., a cell lysate or in a reconstituted system. In other embodiments, the contacting step is detected in a cell in culture, e.g., a cell expressing a RAF1 fusion (e.g., a mammalian cell, a tumor cell or cell line, a recombinant cell). In yet other embodiments, the contacting step is detected in a cell in vivo (e.g., a RAF11 expressing cell present in a subject, e.g., an animal subject (e.g., an in vivo animal model)).

Exemplary parameters evaluated in identifying an agent that modulates the activity of a RAF1 fusion (e.g., an AGGF1:RAF1 fusion, an MPRIP:RAF1 fusion, a PAPD7:RAF1 fusion, an LMNA:RAF1 fusion, a CLCN6:RAF1 fusion, or a TRAK1:RAF1 fusion) include one or more of:

(i) a change in binding activity, e.g., direct binding of the candidate agent to a RAF11 fusion protein; a binding competition between a known ligand and the candidate agent to a RAF1 fusion protein;

(ii) a change in kinase activity, e.g., phosphorylation levels of a RAF1 fusion protein (e.g., an increased or decreased phosphorylation or autophosphorylation) or a change in phosphorylation of a target of a RAF1 kinase—in certain embodiments, a change in kinase activity, e.g., phosphorylation, is detected by any of Western blot (e.g., using an anti-RAF1 antibody or a phosphor-specific antibody, detecting a shift in the molecular weight of a RAF1 fusion protein), mass spectrometry, immunoprecipitation, immunohistochemistry, immunomagnetic beads, among others;

(iii) a change in an activity of a cell containing a RAF1 fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor;

(v) a change in the level, e.g., expression level, of a RAF1 fusion protein or nucleic acid molecule; or (vi) a change in an activity of a signaling pathway involving RAF1, e.g., phosphorylation or activity of an interacting or downstream target, or expression level of a target gene.

Methods for Validating RAF1 Fusions

RAF1 gene fusions (e.g., AGGF1:RAF1 gene fusions, MPRIP:RAF1 gene fusions, PAPD7:RAF1 gene fusions, LMNA:RAF1 gene fusions, CLCN6:RAF1 gene fusions, or TRAK1:RAF1 gene fusions) may be evaluated to ensure that the breakpoints are in-frame and can produce a protein product containing the full kinase domain, i.e., that the breakpoint occurs such that complete triplet codons are intact, and that the RNA sequence will produce a viable protein. The RAF1 gene fusion can be transfected into cells to confirm that the protein is functionally active with respect to kinase activity and oncogenic activity. cDNA encoding the RAF1 fusion protein can be produced by standard solid-phase DNA synthesis. Alternatively the RAF1 fusion cDNA can be produced by RT-PCR using tumor mRNA extracted from samples containing the gene fusion. The DNA amplified can be subcloned into an appropriate vector and characterized by DNA sequence analysis or in vitro/in vivo expression analyses.

Expression vectors containing the RAF1 gene fusion (such as, e.g., a RAF1 gene fusion, e.g., an AGGF1:RAF1 gene fusion, an MPRIP:RAF1 gene fusion, a PAPD7:RAF1 gene fusion, an LMNA:RAF1 gene fusion, a CLCN6:RAF1 gene fusion, or a TRAK1:RAF1 gene fusion) can be introduced into host cells to thereby produce a RAF1 fusion protein (such as, e.g., a RAF1 fusion protein, e.g., an AGGF1:RAF1 fusion protein, an MPRIP:RAF1 fusion protein, a PAPD7:RAF1 fusion protein, an LMNA:RAF1 fusion protein, a CLCN6:RAF1 fusion protein, or a TRAK1:RAF1 fusion protein). The RAF1 fusion protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant RAF1 gene fusion can then be tested for production of the unique fusion protein via standard Western blotting using either an antibody probe that detects the gene product itself or that recognizes a tag peptide (e.g., FLAG tag) that can be added to the gene product via the expression vector (using standard, commercially available reagents). Western blotting can be used to confirm the ectopic expression of the encoded RAF1 fusion protein by comparing the samples from cells transfected with the vector containing the RAF1 gene fusion cDNA to cells transfected with the empty expression vector. The functional activity can be assessed by measuring the level of phosphorylation on the kinase or substrate. Comparison of the level of phosphorylation activity between the wild type (normal) form of RAF1 and the RAF1 fusion protein can indicate if the RAF1 fusion protein has elevated activity that could drive oncogenic activity. Whether the RAF1 gene fusion is oncogenic can be assessed by measuring capacity of the expressed RAF1 fusion protein to transform cells, that is, to enable cells to grow and proliferate under conditions which are not permissive for growth of normal cells. One commonly used method of measuring the transforming activity of a kinase is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of a RAF1 gene fusion (such as, e.g., an AGGF1:RAF1 gene fusion, an MPRIP:RAF1 gene fusion, an LMNA:RAF1 gene fusion, a PAPD7 gene fusion, a CLCN6:RAF1 gene fusion, or a TRAK1:RAF1 gene fusion) and provide a level of validation of a RAF1 fusion protein (such as, e.g., an AGGF1:RAF1 fusion protein, an MPRIP:RAF1 fusion protein, a PAPD7:RAF1 fusion protein, an LMNA:RAF1 fusion protein, a CLCN6:RAF1 fusion protein, or a TRAK1:RAF1 fusion protein) as a potential target for treating patients that harbor these fusions.

A change in an activity of a cell can be detected in a cell in culture. e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

To further validate the biological implication of the gene fusion, a change in any of the activities of the cell, e.g., the recombinant cell, in the presence of a known inhibitor of one of the fusion partners, e.g., a RAF1 inhibitor, can be detected. For example, a decrease in one or more of: proliferation, tumorigenicity, and transformed morphology, in the presence of the BETA inhibitor can be indicative of an inhibitor of a fusion. In other embodiments, a change in binding activity or phosphorylation of RAF1 or its interacting or downstream proteins or molecules is detected.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of"or" means "and/or" unless stated otherwise. The use of the term "including," as well as other forms, such as "includes" and "included," is not limiting. All ranges given in the application encompass the endpoints unless stated otherwise.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting in a patient an AGGF1:RAF1 fusion, said method comprising:

a) contacting a biological sample from the patient with an oligonucleotide that hybridizes to or amplifies an AGGF1:RAF1 fusion junction of SEQ ID NO: 1 and b) detecting binding between the AGGF1:RAF1 fusion and the oligonucleotide or detecting amplification of the AGGF1:RAF1 fusion junction.

2. The method of claim 1, wherein the oligonucleotide hybridizes under stringent conditions to (a) a fragment of SEQ ID NO: 1 comprising nucleotides 866-875 of SEQ ID NO: 1; or (b) a complementary oligonucleotide of (a).

3. The method of claim 1, wherein the patient is suffering from or susceptible to a cancer.

4. The method of claim 3, wherein the cancer is prostate adenocarcinoma or melanoma.

5. The method of claim 4, wherein the cancer is prostate adenocarcinoma.

6. The method of claim 4, wherein the cancer is melanoma.

* * * * *